United States Patent
de la Fuente Gonzalez et al.

(10) Patent No.: US 10,022,400 B2
(45) Date of Patent: Jul. 17, 2018

(54) METHODS OF CAPTURING TUMOR CELLS

(71) Applicants: SERGAS, Santiago de Compostela, La Coruna (ES); University of Santiago de Compostela, Santiago de Compostela, La Coruna (ES); Fundacion Ramon Dominguez, Santiago de Compostela, La Coruna (ES); Fundacion Pedro Barrie de la Maza, Conde de Fenosa, Canton Garde, La Coruna (ES)

(72) Inventors: Alexandre de la Fuente Gonzalez, Santiago de Compostela (ES); Rafael Lopez, Santiago de Compostela (ES); Miguel Abal Posada, Santiago de Compostela (ES)

(73) Assignees: Fundacion Ramon Dominguez, Santiago de Compostela, La Coruna (ES); SERGAS, Santiago de Compostela, La Coruna (ES)

(*) Notice: Subject to any disclaimer, the term of this patent is extended or adjusted under 35 U.S.C. 154(b) by 0 days.

(21) Appl. No.: 14/647,670

(22) PCT Filed: Nov. 26, 2013

(86) PCT No.: PCT/EP2013/074794
§ 371 (c)(1),
(2) Date: May 27, 2015

(87) PCT Pub. No.: WO2014/083019
PCT Pub. Date: Jun. 5, 2014

(65) Prior Publication Data
US 2015/0290245 A1    Oct. 15, 2015

(30) Foreign Application Priority Data

Nov. 27, 2012 (EP) .................................. 12382468
Jan. 29, 2013 (GB) .................................. 1301571.4

(51) Int. Cl.
*A61K 35/12* (2015.01)
*A61K 38/18* (2006.01)
(Continued)

(52) U.S. Cl.
CPC .............. *A61K 35/12* (2013.01); *A61K 35/28* (2013.01); *A61K 35/545* (2013.01); *A61K 38/18* (2013.01);
(Continued)

(58) Field of Classification Search
None
See application file for complete search history.

(56) References Cited

U.S. PATENT DOCUMENTS 4,776,173 A    10/1988    Kamarei
5,153,067 A    10/1992    Eiichi
(Continued)

FOREIGN PATENT DOCUMENTS

WO    WO 03/011330 A1    2/2003
WO    WO 2009/002401 A2    12/2008
(Continued)

OTHER PUBLICATIONS

Harrison, P. "Tumors in Primordial Animals Suggest Cancer Can't Be Prevented", Aug. 26, 2014, accessed at www.medscape.com.*
(Continued)

*Primary Examiner* — Carlos A Azpuru
*Assistant Examiner* — Casey S Hagopian
(74) *Attorney, Agent, or Firm* — Nixon Peabody LLP; Mark J. FitzGerald; Srividya Subramanian

(57) ABSTRACT

The present invention relates to a composition for modulating tumor cell dissemination, in particular metastatic cancer cells. In particular, the invention relates to an agent for modulating metastatic tumor cell dissemination for use in the treatment and/or prevention of a metastatic cancer
(Continued)

Figure 1:
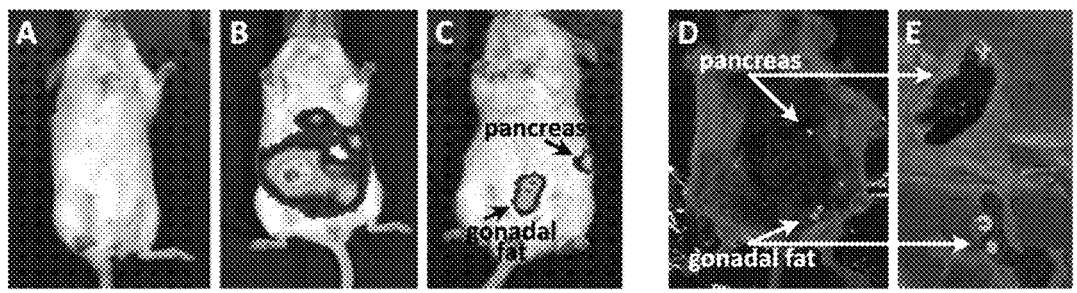

wherein the agent is a capture agent and/or a chemoattractant for tumor cells. The invention also relates to a product, comprising an agent for modulating metastatic tumor cell dissemination, and to a method of treatment or prevention of cancer.

7 Claims, 11 Drawing Sheets

(51) Int. Cl.
  A61K 35/545 (2015.01)
  A61K 38/39 (2006.01)
  A61K 35/28 (2015.01)
  A61K 38/19 (2006.01)
  A61K 39/00 (2006.01)
  A61K 45/06 (2006.01)

(52) U.S. Cl.
  CPC ...... A61K 38/1808 (2013.01); A61K 38/1825 (2013.01); A61K 38/1841 (2013.01); A61K 38/19 (2013.01); A61K 38/39 (2013.01); A61K 39/0011 (2013.01); A61K 45/06 (2013.01)

(56) References Cited

U.S. PATENT DOCUMENTS

| | | | |
|---|---|---|---|
| 7,803,395 B2 * | 9/2010 | Datta | A61L 27/18 424/426 |
| 2010/0159008 A1 | 6/2010 | Barron | |
| 2010/0318108 A1 * | 12/2010 | Datta | A61L 31/10 606/151 |
| 2011/0020216 A1 * | 1/2011 | Mooney | A61L 27/50 424/1.11 |
| 2014/0007510 A1 | 1/2014 | Salzmann | |

FOREIGN PATENT DOCUMENTS

| WO | 2011/090778 A1 | 7/2011 |
|---|---|---|
| WO | WO 2012/019049 A1 | 2/2012 |
| WO | 2014/063128 A1 | 4/2014 |
| WO | 2014/083019 A2 | 6/2014 |

OTHER PUBLICATIONS

Williamson, P., "Exercise for Special Populations", 2011, Lippincott Williams & Wilkins, 1st Ed., p. 350.*
Anonymous, "Q&A: Caught in a trap—UT Arlington Inquiry Magazine (2012)," Inquiry—The Research Magazine for the Universoty of Texas at Arlington, Sep. 20, 2012, http://www.uta.edu/ucomm/researchmagazine/2012/cancer/caught-in-a-trap.php, (retrieved Oct. 21, 2015).
International Preliminary Report on Patentability, PCT appl. No. PCT/EP2013/074794, 12 pages (dated Jun. 2, 2015).
International Search Report, PCT appl. No. PCT/EP2013/074794, 9 pages (dated Jun. 2, 2014).
Mignot et al., "Prospects for exosomes in immunotherapy of cancer," J. Cell. Mol. Med. 10(2):376-388 (2006).
Silk and Sigman, "Effect of Pluronic-F68 on the Development of Tumor Metastasis," Cancer 29(1):171-172 (1972).
Tang, "Development of cancer traps for prolonging lifespan by eliminating metastatic cancer cells," Cancer Prevention and Research Institute of Texas, Nov. 3, 2011, http://www.cprit.state.tx.us/files/funded-grants/RP120572.pdf, (retrieved Oct. 21, 2015).
Written Opinion of the International Searching Authority, PCT appl. No. PCT/EP2013/074794, 11 pages (dated Jun. 2, 2014).
Ahmed et al., "Role of integrin receptors for fibronectin, collagen and laminin in the regulation of ovarian carcinoma functions in response to a matrix microenvironment", Clin Exp Metastasis 22(5) 391-402 (2005).
Burleson et al., "Ovarian carcinoma ascites spheroids adhere to extracellular matrix components and mesothelial cell monolayers", Gynecol Oncol 93(1) 170-181 (2004).
Caicedo-Carvajal et al., "Cancer Tissue Engineering: A Novel 3D Polystyrene Scaffold for In Vitro Isolation and Amplification of Lymphoma Cancer Cells from Heterogeneous Cell Mixtures", J Tissue Eng 2011:362326 (2011). 10 pp.
Cao et al., "Electrospun nanofibers as a bioadhesive platform for capturing adherent leukemia cells", J Biomed MAter Res 102(2) 523-531 (2014).
Damanik et al., "Towards an in vitro model mimicking the foreign body response: tailoring the surface properties of biomaterials to modulate extracellular matrix", Sci Res 4:6325 (2014).
De La Fuente et al., "M-Trap: Exosome-Based Capture of Tumor Cells as a New Technology in Peritoneal Metastasis", J Natl Cancer Inst 107(9) (2015). 10 pp.
De Vlieghere et al., "Tumor-environment biomimetics delay peritoneal metastasis formation by deceiving and redirecting disseminated cancer cells", Biomaterials, 54:148-57 (2015).
Frantz et al., "The extracellular matrix at a glance", J Cell Sci, 123(Pt 24):4195-4200 (2010).
Guo et al., "Controllable metastasis: the trap for the esophageal cancer cells?", Med Hypotheses, 74(6):1000-1 (2010).
Hou et al., "Collagen attachment to the substrate controls cell clustering through migration", Phys Biol, 11(5):056007 (2014) 13pp.
Jain et al., "Guiding intracortical brain tumour cells to an extracortical cytotoxic hydrogel using aligned polymeric nanofibres", Nat Mater, 13(3):308-316 (2014).
Karagiannis et al., "Cancer-associated fibroblasts drive the progression of metastasis through both paracrine and mechanical pressure on cancer tissue", Mol Cancer Res, 10(11):1403-1418 (2012).
Ko et al., "The use of chemokine-releasing tissue engineering scaffolds in a model of inflammatory response-mediated melanoma cancer metastasis", Biomaterials, 33(3):876-885 (2012).
Levental et al., "Matrix crosslinking forces tumor progression by enhancing integrin signaling", Cell, 139(5):891-906 (2009).
Liang et al., "Rapid adherence to collagen IV enriches for tumour initiating cells in oral cancer", Eur J Cancer, 50 (18):3262-3270 (2014).
Lu et al., "Isolation of circulating epithelial and tumor progenitor cells with an invasive phenotype from breast cancer patients", Int J Cancer, 126(3):669-683 (2010).
Ma et al., "Trap Effect of Three-Dimensional Fibers Network for High Efficient Cancer-Cell Capture", Adv Healthc Mater, 4(6):838-43 (2015).
Madhavan et al., "Evaluation of composition and crosslinking effects on collagen-based composite constructs", Acta Biomater, 6(4):1413-1422 (2010).
McIntosh, et al., "Control of Mammalian Cell Behaviour Through Mimicry of the Extracellular Matrix Environment", INTECH Open Access Publisher (2011) 20pp.
Moreau et al., "Tissue-engineered bone serves as a target for metastasis of human breast cancer in a mouse model", Cancer Res, 67(21):10304-10308 (2007).
Rizwan et al., "Metastatic breast cancer cells in lymph nodes increase nodal collagen density", Sci Rep, 5:10002 (2015).
Seib et al., "Tissue engineering a surrogate niche for metastatic cancer cells", Biomaterials, 51:313-319 (2015).
Anonymous: "Biomerix 3D Scaffold (TM)", XP055204491; retrived from http://cellon.lu/wa_files/Biomerix_20Scaffold_20Brochure.pdf, Jan. 1, 2010.
Merzak et al., "CD44 mediates human glioma cell adhesion and invasion in vitro." Cancer Research 54 (15):3988-3992 (1994).
Zaman et al. "Migration of tumor cells in 3D matrices is governed by matrix stiffness along with cell-matrix adhesion and proteolysis." PNAS 103(29):10889-10894 (2006).

* cited by examiner

METHODS OF CAPTURING TUMOR CELLS

The present invention relates to an agent for modulating the dissemination of cancer cells, in particular metastatic cancer cells, and to the use of the agent in the treatment or prevention of cancer. The composition may capture and/or attract cancer cells, in particular metastatic cancer cells. The invention also relates to a method of treatment or prevention of cancer.

The process of metastasis is associated with more than 90% of cancer-related deaths and represents the main challenge in oncology. While primary disease is reasonably accessible to surgery and/or radiotherapy and presents an acceptable response to chemotherapy leading to a good prognosis; metastatic dissemination is associated with a contraindication to surgery and radiotherapy and especially resistance to chemotherapy, and offers a much worse prognosis.

In recent years, the process of metastasis has been characterized as a stepwise process where aggressive tumor cells acquire the abilities to invade the surrounding stroma and tissues, to intravasate and survive in the blood flow, and to extravasate and generate a micrometastasis at distant organs. In general, there are two main ways of tumor cell dissemination from the primary lesion: systemic dissemination of metastatic tumor cells through the blood and lymphatic vessels, and loco-regional dissemination by release or migration/invasion of metastatic tumor cells into the surroundings. Tumor cells which disseminate from the primary tumor into the bloodstream, are known as circulating tumor cells (CTC), and are the main cause of metastasis. For dissemination through blood and lymphatic vessels, the consensus is that tumor cells must acquire an aggressive phenotype allowing migration and invasion of the surrounding stroma (epithelial to mesenchymal transition); activate neoangiogenesis by attracting endothelial cells and creating new blood vessels that provide the tumor not only with nutrients but also generating routes for dissemination; then tumor cells invade and incorporate into the new blood vessels (intravasation) and disseminate to those sites in the organism where they will attach and exit the blood vessels (extravasation); finally, these metastatic tumor cells will be able to establish a niche and generate a micrometastasis that will evolve into a metastatic lesion. The whole process is extremely inefficient but dramatically lethal. Alternatively, dissemination may occur through cellular migration and invasion of the surrounding stroma and organs, or like in ovarian cancer where tumor cells are exposed and released to the peritoneal cavity, by incorporation of metastatic cells into the ascitic fluid and implantation in the peritoneum and organs accessible in the cavity.

The molecular and cellular bases that determine the process of metastasis suggest an intense dialogue of the primary tumor with the environment (Sleeman, J P et al., Semin Cancer Biol. 2012 June; 22(3):174-86). Tissue specific metastasis (Nguyen et al., Nat Rev Cancer. 2009; 9(4):274-84) and pre-metastatic niches (Psaila & Lyden, Nat Rev Cancer. 2009; 9(4):285-93) are concepts that are beginning to illustrate an active role of carcinomas in the determination of the most adequate sites to colonize: signals emitted from the tumor and from the environment may govern the remodeling of targeted tissues for a favored reception of tumor cells disseminated from primary lesions.

An aim of the present invention is to interfere with the communication between tumor cells, and in particular metastatic tumor cells, and the host, to allow the pattern of metastatic dissemination to be modulated. The invention may operate, in certain embodiments, by physically trapping such cells and/or by providing a preferential site for homing of such cells.

According to a first aspect, the invention provides an agent for modulating tumor cell dissemination for use in the treatment and/or prevention of a cancer.

The invention also provides the use of an agent for modulating tumor cell dissemination in the treatment and/or prevention of cancer.

The invention also further provides the use of an agent for modulating tumor cell dissemination in the preparation of a medicament for the treatment and/or prevention of cancer.

Preferably the agent for modulating tumor cell dissemination is for modulating metastatic tumor cell dissemination. Preferably the agent is for use in the treatment and/or prevention of a metastatic cancer.

The agent for modulating tumor cell dissemination may act to interfere with the natural process of tumor cell dissemination, preferably to modulate the behavious of such cells such that they are attracted to or captured at a particular site, preferably at the location of the agent for modulating tumor cell dissemination.

The agent for modulating tumor cell dissemination may be a capture agent and/or a chemoattractant for tumor cells, in particular for metastatic tumor cells. The metastatic tumor cells may be circulating tumor cells, disseminated tumor cells or any cell disseminated from a primary tumor.

The agent for modulating tumor cell dissemination may be a capture agent intended to capture or trap tumor cells, and in particular metastatic tumor cells, such as circulating tumor cells, disseminated tumor cells or any cell disseminated from a primary tumor. The capture agent may directly mediate capture of the tumor cells, for example by adhering to the tumor cells, or may have an indirect effect which improves adhesion of the tumor cells at specific sites in the host.

A capture agent for use in the invention may be a material which is capable of physically capturing tumor cells and trapping them, the capture agent may be an adhesive material to which tumor cells adhere.

The capture agent may capture/trap the cells by providing a favoured substrate for the metastatic cells to attach and anchor to. This substrate may be a solid 2D or 3D polymer surface, or a chemically modified surface, or a patterned surface, or a gel, or a hydrogel, etc, where the cell can create adhesive structures such as focal adhesions, tight junctions, anchoring junctions, GAP junctions, etc.

The capture agent may be a 2D or a 3D porous structure. In one embodiment the capture agent may be a 3D porous tissue scaffold type material. The capture agent may be a 3D porous mesh structure.

The capture agent may be made from one or more of many different materials, including natural and synthetic materials; and biodegradable and permanent materials. Many such materials are well known, and indeed many have been used in the medical field. Examples of synthetic polymers suitable for use as the capture agent of the present invention include: poly (alpha-hydroxyacids) especially polylactic acids (PLA) or polyglycolic acids (PGA), poly-lactide poly-glycolide copolymers, poly-lactide polyethylene glycol (PEG) copolymers; other polyesters including polycaprolactones, such as poly (epsilon-caprolactone), poly (3-hydroxybutyrate), poly (s-caproic acid), poly (p-dioxanone) and poly (propylene fumarate); poly (ortho esters) including polyol/diketene acetals addition polymers; polyanhydrides including poly (sebacic anhydride) (PSA), poly (carboxybiscarboxyphenoxyphenoxyhexane) (PCPP), poly

[bis (p-carboxyphenoxy) methane] (PCPM) and copolymers of SA, CPP and CPM; poly (amino acids); poly (pseudo amino acids); polyphosphazenes including derivatives of poly [(dichloro) phosphazene]; poly [(organo) phosphazenes] polymers; polystyrenes; polyurethanes; polycarbonates; polyphosphates; polyethylene glycol polypropylene block co-polymers; poloxamers such as Pluronic™. Such polymers may be used to produce 3D porous carriers. Alternatively, or additionally, natural polymers may also be used, such as silk, elastin, chitin, chitosan, fibrin, fibrinogen, natural gums (such xanthan), polysaccharides (including pectins), alginates, collagen, poly (amino acids), peptides, polypeptides or proteins. Again, such polymers may be used to produce 3D porous carriers. Co-polymers prepared from the monomers of any of the above polymers may also be used, as may random blends of the polymers or mixtures or combinations thereof.

The capture agent may be in the form of a hydrogel.

In one embodiment the capture agent may comprise polystyrene and/or polycaprolactone. The polystyrene and/or polycaprolactone may be used to produce a 3D porous structure, such as a porous mesh. For example, the invention may use a 3D InsertTM-PS Nanomesh™ Tissue Culture Scaffold provided by 3D Biotek™, New Jersey, USA. In an alternative embodiment the capture agent comprises an alginate sponge, such as the AlgiMatrix™ 3D Culture System from Gibco™. In a further embodiment the capture agent may be a polycarbonate polyurethane with urea cross-links, such as the Biomerix™ 3D Scaffolds from Sigma Aldrich, USA.

Where the capture agent comprises a solid surface the surface may be made of, decorated with or have embedded therein adhesion molecules to improve the attachment of tumor cells, and metastatic tumor cells in particular, to the surface. The adhesion molecules may be proteins or other molecules which mediate cell-cell adhesion or cell-substrate adhesion, like CAMs, cadherins, integrins, selectins, tetraspanins, extracellular matrix proteins, RGD-peptides or modified-peptides that may improve cell adhesion, or a protein or molecule that promotes cell adhesion. In addition, the capture agent may capture/trap the metastatic cells by remodeling the site of implantation of the invention, by means of remodeling the cellular architecture of the site of implantation, or by remodeling the extracellular matrix, by remodeling the site through a foreign body reaction (Anderson et al., Semin Immunol 2008) or an inflammatory reaction.

Alternatively the adhesion molecules may be the capture agent, preferably without a solid surface.

The agent for modulating tumor cell dissemination may alternatively or additionally be a chemoattractant for tumor cells, and in particular metastatic tumor cells, such as circulating tumor cells, disseminated tumor cells or any cell disseminated from a primary tumor.

In some embodiments the agent for modulating tumor cell dissemination may act as both a capture agent and a chemoattractant for tumor cells.

Useful chemoattractants may be any agent capable of attracting tumor cells, and in particular metastatic tumor cells, such as circulating tumor cells, disseminated tumor cells or any cell disseminated from a primary tumor. The tumor cells may be attracted directly or indirectly through the attraction of an intermediate cell (i.e. immune cell or stem cell). For example, the implantation of an agent of the invention may generate an inflammatory reaction that provides an additional chemotactic effect for metastatic cancer cells.

The agent for modulating tumor cell dissemination, such as the capture agent and/or chemoattractant, may comprise vesicles derived from cells, including exosomes. Exosomes are cell-derived microvesicles that are present in many and perhaps all biological fluids, including blood, urine, and ascitic fluid. They typically have a diameter of between 30 and 100 nm. They are released by many cells types during normal physiological processes; however tumors appear to aberrantly secrete large quantities of exosomes. Exosomes for use in the invention may be obtained from a bodily fluid, such as blood or urine, or obtained from many different cell types in an organism. The bodily fluid from which exosomes are purified may be from a healthy donor. Exosomes for use in the invention may be secreted by cancer cells, such as ovarian cancer cells; or alternatively, or in addition, the exosomes may be secreted by non cancer cells, such as mesenchymal stem cells. It may be preferable to use exosomes from non cancer cells Alternatively, or additionally, the agent for modulating tumor cell dissemination may be ascitic fluid from a subject with ovarian cancer. The ascitic fluid may comprise exosomes. The capture agent or chemoattractant may be exosomes obtained from the ascitic fluid of a subject with ovarian cancer.

Alternatively, or additionally, the agent for modulating tumor cell dissemination may be mesenchymal stem cells themselves, or indeed another form of stem cells, but preferably not human embryonic stem cells. Mesenchymal stem cells of adipose, umbilical cord or bone marrow origin may be used as a chemoattractant.

Alternatively or additionally, the agent for modulating tumor cell dissemination may be a cell adhesion molecule, such as a selectin, a member of the immunoglobulin (Ig) superfamily, an integrin or a cadherin. The cell adhesion molecule may be found associated with exosomes such as CD9 and/or CD81.

Alternatively, or additionally, the agent for modulating tumor cell dissemination may comprise one or more chemokines and/or one or more growth factors, for example one or more of SDF1, 90K, osteopontin, EGF, TGFb1, FGF, and IGF. In one embodiment the chemoattractant comprises a combination of EGF, TGFb1 and FGF.

Alternatively, or additionally, the agent for modulating tumor cell dissemination may comprise one or more extracellular matrix proteins, for example, fibronectin or collagen.

The agent for modulating tumor cell dissemination may be contained in and/or attached to a carrier.

The agent for modulating tumor cell dissemination may be physically or chemically contained within or attached to a carrier. The agent for modulating tumor cell dissemination may be permanently contained within the scaffold or may be released in a controlled or uncontrolled manner from the carrier.

If used with a carrier, the chemoattractant and/or capture agent may remain attached to or within the carrier, or may be released or leached from the carrier to create a gradient of chemoattractant and/or capture agent around the carrier.

The carrier may be any suitable material that is able to carry, either by containing or having attached thereto, the agent for modulating tumor cell dissemination. The agent for modulating tumor cell dissemination may be a capture agent and/or chemoattractant.

The carrier may itself be an agent for modulating tumor cell dissemination, such as a capture agent and/or a chemoattractant.

The carrier is preferably biocompatible, such that if placed in a human or non-human animal it does not cause an unacceptable immune response. In some embodiments the carrier may be associated with a limited immune response at the site of placement, for example an inflammatory immune response or foreign body reaction.

The carrier may be porous. The carrier may be a 2D or a 3D porous structure. In one embodiment the carrier may be a 3D porous tissue scaffold type material. The carrier may be a 3D porous mesh structure.

The carrier may be made from one or more of many different materials, including natural and synthetic materials; biodegradable and permanent materials. Many such materials are well known, and indeed many have been used in the medical field Examples of synthetic polymers suitable for use in the carrier of the present invention include: poly (alpha-hydroxyacids) especially polylactic acids (PLA) or polyglycolic acids (PGA), poly-lactide poly-glycolide copolymers, poly-lactide polyethylene glycol (PEG) copolymers; other polyesters including polycaprolactones, such as poly (epsilon-caprolactone), poly (3-hydroxybutyrate), poly (s-caproic acid), poly (p-dioxanone) and poly (propylene fumarate); poly (ortho esters) including polyol/diketene acetals addition polymers; polyanhydrides including poly (sebacic anhydride) (PSA), poly (carboxybiscarboxyphenoxyphenoxyhexane) (PCPP), poly [bis (p-carboxyphenoxy) methane] (PCPM) and copolymers of SA, CPP and CPM; poly (amino acids); poly (pseudo amino acids); polyphosphazenes including derivatives of poly [(dichloro) phosphazene]; poly [(organo) phosphazenes] polymers; polystyrenes; polyurethanes; polycarbonates; polyphosphates; polyethylene glycol polypropylene block copolymers; poloxamers such as Pluronic™. Such polymers may be used to produce 3D porous carriers.

Alternatively, or additionally, natural polymers may also be used, such as silk, elastin, chitin, chitosan, fibrin, fibrinogen, natural gums (such xanthan), polysaccharides (including pectins), alginates, collagen, poly (amino acids), peptides, polypeptides or proteins. Again, such polymers may be used to produce 3D porous carriers.

Co-polymers prepared from the monomers of any of the above polymers may also be used, as may random blends of the polymers or mixtures or combinations thereof.

The carrier may be in the form of a hydrogel.

In one embodiment the carrier may comprise polystyrene and/or polycaprolactone. The polystyrene and/or polycaprolactone may be used to produce a 3D porous structure, such as a porous mesh. For example, the invention may use a 3D InsertTM-PS Nanomesh™ Tissue Culture Scaffold provided by 3D Biotek™, New Jersey, USA.

In an alternative embodiment the carrier comprises an alginate sponge, such as the AlgiMatrix™ 3D Culture System from Gibco™.

In a further embodiment the carrier may be a polycarbonate polyurethane with urea crosslinks, such as the Biomerix™ 3D Scaffolds from SIGMA ALDRICH, USA.

The carrier may be a soluble or dissolvable material, or at least partially soluble or partially dissolvable.

The carrier may be a recipient of the agent for modulating tumor cell dissemination whose function is to create a gradient of the agent, essentially by releasing the agent over time. The agent may be released in a controlled or an uncontrolled manner. Release of the agent may be active or passive, or both.

Preferably the carrier, in use, retains at least 10%, 20% 30%, 40%, 50% or more of the agent for at least 12 hours, at least 24 hours, at least 48 hours, at least 3 days, at least 4 days, at least 5 days, at least 6 days, at least 1 week, at least 2 weeks, at least 3 weeks, at least 4 weeks or longer.

Preferably the carrier, in use, releases at least 10%, 20% 30%, 40%, 50% or more of the agent over at least 12 hours, at least 24 hours, at least 48 hours, at least 3 days, at least 4 days, at least 5 days, at least 6 days, at least 1 week, at least 2 weeks, at least 3 weeks, at least 4 weeks or longer.

Preferably the carrier, in use, creates an agent gradient for at least 12 hours, at least 24 hours, at least 48 hours, at least 3 days, at least 4 days, at least 5 days, at least 6 days, at least 1 week, at least 2 weeks, at least 3 weeks, at least 4 weeks or longer.

Preferably the carrier of the invention is able to release sufficient agent for modulating tumor cell dissemination to generate a gradient of agent effective for loco-regional dissemination and/or for systemic dissemination in a subject for a period sufficient to avoid metastatic dissemination. Preferably the agent is a chemoattractant and the product of the invention is able to attract tumor cells for a sustained period. Preferably the product of the invention is able to attract tumor cells for at least 1 day, at least 2 days, at least 3 days, at least 4 days, at least 5 days, at least 6 days, at least 1 week, at least 2 weeks, at least 3 weeks, at least 4 weeks or longer.

The agent for modulating tumor cell dissemination may be encapsulated in liposomes or nano/microparticles or modified cellular vesicles like exosome-mimetic vesicles. Soluble tablets and/or capsules may also be used to contain or carry (by way of attachment) the agent for modulating tumor cell dissemination. The tablets and/or capsules may be configured to selectively release the agent for modulating tumor cell dissemination at a desired site. Examples of polymers which may be used to form tables or capsules include but are not limited to cellulose acetate phthalate, hydroxypropylmethylcellulose phthalate, polyvinylacetate phthalate, hydroxypropylmethylcellulose phthalate, methacrylic acid copolymer, shellac, methylcellulose phthalate, cellulose acetate trimellitate, hydroxypropylmethylcellulose acetate succinate, cellulose acetate phthalate, cellulose acetate succinate, cellulose acetate malate, cellulose benzoate phthalate, cellulose propionate phthalate, carboxymethylethylcellulose, ethylhydroxyethylcellulose phthalate, shellac, styrene-acrylic acid copolymer, methyl acrylate-acrylic acid copolymer, methyl acrylate-methacrylic acid copolymer, butyl acrylate-styrene-acrylic acid copolymer, methacrylic acid-methyl methacrylate copolymer, methacrylic acid-ethyl acrylate copolymer, methyl acrylate-methacrylic acid-octyl acrylate copolymer, vinyl acetate-maleic acid anhydride copolymer, styrene-maleic acid anhydride copolymer, styrene-maleic acid monoester copolymer, vinyl methyl ether-maleic acid anhydride copolymer, ethylene-maleic acid anhydride copolymer, vinyl butyl ether-maleic acid anhydride copolymer, acrylonitrile-methyl acrylate-maleic acid anhydride copolymer, butyl acrylate-styrene-maleic acid anhydride copolymer, polyvinyl alcohol phthalate, polyvinyl acetal phthalate, polyvinyl butylate phthalate and polyvinyl acetoacetal phthalate, or combinations thereof. The material encapsulating the agent for modulating tumor cell dissemination may dissolve when administered allowing release of the agent for modulating tumor cell dissemination. In an embodiment the capsule may be a soft gelatin capsule.

The carrier may be a bodily tissue or fluid, for example, the carrier may be body fat.

The agent for modulating tumor cell dissemination may be in a liquid or powder form, or in any other suitable form. The chemoattractant may be in a lyophilized form.

In a further aspect the invention provides a product comprising a carrier and an agent for modulating tumor cell metastatic dissemination wherein the agent for modulating tumor cell metastatic dissemination is contained in and/or attached to the carrier.

The product may comprise a carrier as described herein, and the agent for modulating tumor cell metastatic dissemination may be as described herein.

The product may contain, for example, from about 10% to about 98% by weight, preferably about 80%, preferably at least about 20%, 25%, 30%, 35%, 40%, 45%, 50% or more by weight of the agent for modulating tumor cell dissemination.

The product may contain between 0.1 nanograms and 10 mg of an agent for modulating tumor cell dissemination, such as a capture agent and/or chemoattractant. Preferably between 0.1 nanograms and 1 mg, or 0.1 nanograms and 100 micrograms of the agent for modulating tumor cell dissemination, such as a capture agent and/or chemoattractant.

In addition to the agent for modulating tumor cell dissemination, the product of the invention may further comprise a chemotherapeutic agent, such as a cytostatic agent.

Wherein a cytostatic agent is a pharmacologically active compound capable of inhibiting or suppressing cellular growth and multiplication. Depending on the mechanism of action and on the dose of the compound, it may also represent a cytotoxic agent. In particular, the cytostatic agent may be a compound is capable of killing, or inhibiting the growth of, tumor cells, preferably metastatic tumor cells, such as circulating tumor cells, disseminated tumor cells or any cell disseminated from a primary tumor.

The cytostatic agent may be selected, for example, from:
(a) anthracyclines and analogs thereof, such as daunomycin, doxorubicin, idarubicin, epirubicin, valrubicin, aclacinomycin, and mitoxantrone;
(b) antimetabolites, such as gemcitabine, cytosine arabinoside, cytarabine, vidarabine, thioguanine, pentostatin, cladribine, methotrexate, floxuridine, fluorouracil and other fluorinated pyrimidines, purines, or nucleosides;
(c) alkylating agents, such as nitrogen mustards, including cyclophosphamide, melphalan, chlorambucil, ifosfamide; nitrosoureas, including carmustine, lomustine, and streptozocin; alkyl sulfonates, including busulfan; thiotepa; platinum compounds, including cisplatin, carboplatin, oxaliplatin, nedaplatin, satraplatin, and triplatin tetranitrate; procarbazine; and altretamine;
(d) plant alkaloids and terpenoids, such as vinca alkaloids, including vincristine, vinblastine, vinorelbine, and vindesine; taxanes, including taxol, paclitaxel, docetaxel; and podophyllotoxin;
(e) topoisomerase inhibitors, such as amsacrine, etoposide, etoposide phosphate, teniposide and other derivatives of epipodophyllotoxins; irinotecan, topotecan and other camptothecins; and
(f) other antineoplastics, such as dactinomycin, bleomycin, mitomycin, etoposide, bleomycin, and plicamycin.

The agent for modulating tumor cell dissemination may be used alone or in combination with other active agents, for example in combination with one or more cytostatic agents.

The agent for modulating tumor cell dissemination or a product of the invention may be intended for administration by any known method, for example enteral administration, such as oral or rectal, or parenteral administration, for example by injection, or by surgery.

In a preferred embodiment the agent for modulating tumor cell dissemination or a product of the invention is placed at a site of use by surgery. If the agent for modulating tumor cell dissemination or a carrier for the agent for modulating tumor cell dissemination is a 3D mesh or scaffold then it may be administered by surgery.

Alternatively, the agent for modulating tumor cell dissemination or a product of the invention may be placed at a site of use by injection, in this case, if a carrier is used, the carrier must be injectable, for example a hydrogel or alginate material.

The agent for modulating tumor cell dissemination or a product of the invention may be intended for use with many types of cancer, including, but not limited to, breast cancer, colorectal cancer, pancreatic cancer, kidney cancer, prostate cancer, urothelial cancer, oesophageal cancer, head and neck cancer, hepatocellular cancer, mesothelioma, Kaposi's sarcoma, ovarian cancer, soft tissue sarcoma, glioma, melanoma, small-cell and non-small-cell lung cancer, endometrial cancer, basal cell carcinoma, transitional cell carcinoma of the urothelial tract, cervical cancer, endometrial cancer, gastric cancer, bladder cancer, uterine sarcoma, multiple myeloma, soft tissue and bone sarcoma, cholangiocarcinoma and cancers disseminated therefrom.

In particular, the agent for modulating tumor cell dissemination or a product of the invention may be intended for use with cancers of the peritoneal cavity, such as, stomach, gall bladder, liver, small intestine, GIST, esophagus, abdominal sarcoma, soft tissue sarcoma, mesothelioma, ovarian, pancreatic, colon, rectal, uterine, cervical, kidney cancer and cancers disseminated therefrom. In a preferred embodiment the cancer is ovarian cancer or a cancer disseminating therefrom. Where the cancer is ovarian cancer or a cancer disseminating therefrom, the product of the invention may be implanted in the abdominal wall of the subject. Alternatively the cancer may be colon cancer. The cancer may be pancreatic cancer.

The present invention may be intended for use in the prevention of cancer metastases, in particular for the prevention of peritoneal metastases.

According to another aspect, the invention provides the use of a capture agent for trapping tumor cells in the preparation of a medicament for the treatment or prevention of cancer.

According to another aspect the invention provides the use of a chemoattractant of tumor cells in the preparation of a medicament for the treatment or prevention of cancer.

Preferably the treatment or prevention of cancer comprises the attraction and/or trapping of tumor cells, and in particular metastatic tumor cells, such as circulating tumor cells, disseminated tumor cells or any cell disseminated from a primary tumor.

Preferably the attracted cells are held or trapped by the action of the agent for modulating tumor cell dissemination, the capture agent and/or chemoattractant, thus localizing them to a particular location and allowing them to be treated.

Preferably the agent for modulating tumor cell dissemination is provided contained in, or attached to, a carrier as described herein. In some embodiments the carrier itself may be an agent for modulating tumor cell dissemination capable of attracting and/or trapping tumor cells, and the provision of a further capture agent and/or chemoattractant is optional. In some embodiments the agent for modulating tumor cell dissemination is a 3D polymer scaffold, hydrogel or a poloxamer polymer. Such polymer carriers have been found to have adhesive properties and to be capable of trapping tumor cells, e.g. by providing a niche to which such cells can adhere, and/or by providing a preferential site for homing of such cells.

The agent for modulating tumor cell dissemination, capture agent and/or chemoattractant may be any suitable agent, in particular it may be any of the aforementioned capture agents and/or chemoattractants. In an embodiment the agent for modulating tumor cell dissemination, the capture agent and/or chemoattractant comprises exosomes. In another embodiment the agent for modulating tumor cell dissemination, the capture agent and/or chemoattractant comprises a cross-linked, polycarbonate polyurethane-urea matrix (3D-Kube Biomerix scaffold) decorated with an adhesion molecule, such as collagen and/or fibronectin.

Alternatively the agent for modulating tumor cell dissemination, capture agent and/or chemoattractant may be administered on its own, for example into body tissue, where it is retained long enough to be effective. The invention may provide the administration of more than one capture agent and/or more than one chemoattractant. The more than one capture agents and/or the more than one chemoattractants may be administered simultaneously, sequentially or separately.

Preferably the agent for modulating tumor cell dissemination, capture agent and/or the chemoattractant, alone or in a product of the invention, is administered to a non-vital organ. Thus the tumor cells will be attracted to and retained in this tissue and may then be removed by surgery. Such a location may allow the chemoattractant to be accessible from everywhere in the body; for example, it would allow the product of the invention to become vascularized and thus allow the chemoattractant to reach the blood circulation.

Alternatively the agent for modulating tumor cell dissemination, capture agent or the chemoattractant, alone or in a product of the invention, may be administered into the fat of a subject.

In a yet further embodiment the agent for modulating tumor cell dissemination, capture agent and/or the chemoattractant, alone or in a product of the invention, may be administered into the peritoneum of a subject to attract and/or capture metastatic cells disseminating in the peritoneal cavity. Similarly, the pleura may be a good place to locate the agent for modulating tumor cell dissemination, capture agent and/or the chemoattractant when treating lung carcinomas and mesiotheliomas or tumor cells disseminating into the pleura.

The agent for modulating tumor cell dissemination, capture agent and/or the chemoattractant may be administered by direct injection into the fat of a human or non-human animal. For example, for the attraction of peritoneal metastatic tumor cells the agent for modulating tumor cell dissemination, capture agent and/or the chemoattractant may be injected into the peritoneum or surrounding tissue including fat tissue, for example, the gonadal fat.

Preferably, once in situ, the agent for modulating tumor cell dissemination, capture agent and/or chemoattractant causes tumor cells, and in particular metastatic tumor cells, such as circulating tumor cells, disseminated tumor cells or any cell disseminated from a primary tumor, to be attracted to it, and to congregate or be "trapped". In a preferred embodiment the attracted cells are held or trapped by the action of the agent for modulating tumor cell dissemination, capture agent and/or the chemoattractant until the cells are treated. Preferably at least 5%, 10%, 20%. 30%, 40%, 50%, 60%, 70%, 75%, 80%, 85%, 90%, 95%, 98%, 99% or more of the attracted cells are captured by the product of the invention.

The attracted or trapped cells may then be treated. The attracted or trapped cells may be treated by physically removing them, for example by surgery, or by treating them to destroy or inactivate the cells, for example by chemotherapy or radiotherapy. If the carrier includes a cytostatic or cytotoxic agent, or the agent for modulating tumor cell dissemination is administered with a cytostatic or cytotoxic agent, then this may act to eradicate or prevent the replication of the attracted cells.

The tumor cells to be treated may be one or more of any of the cancers described above, in particular, the tumor cells may be derived from/disseminated from a peritoneal cancer, such as ovarian cancer.

According to another aspect the invention provides a method of attracting tumor cells, and in particular metastatic tumor cells, such as circulating tumor cells, disseminated tumor cells or any cell disseminated from a primary tumor, in a subject comprising administering to the subject an agent for modulating tumor cell dissemination, and in particular metastatic tumor cells, such as circulating tumor cells, disseminated tumor cells or any cell disseminated from a primary tumor. The agent for modulating tumor cell dissemination may be provided contained within or attached to a carrier as described with reference to any aspect of the invention. Preferably the attracted cells are retained or trapped by the action of the agent for modulating tumor cell dissemination. Once trapped by the agent for modulating tumor cell dissemination the cancer cells themselves may act as a capture agent and/or chemoattractant for other cancer cells.

According to another aspect the invention provides a method of attracting tumor cells, and in particular metastatic tumor cells, such as circulating tumor cells, disseminated tumor cells or any cell disseminated from a primary tumor, in a subject comprising administering to the subject a chemoattractant of tumor cells, and in particular metastatic tumor cells, such as circulating tumor cells, disseminated tumor cells or any cell disseminated from a primary tumor. The chemoattractant may be provided contained within or attached to a carrier as described with reference to any aspect of the invention. Preferably the attracted cells are retained or trapped by the action of the chemoattractant. Once the attracted cells are trapped they may then act as a capture agent and/or chemoattractant for other cancer cells.

According to another aspect the invention provides a method of attracting tumor cells, and in particular metastatic tumor cells, such as circulating tumor cells, disseminated tumor cells or any cell disseminated from a primary tumor, in a subject comprising administering to the subject a capture agent for trapping tumor cells. The capture agent may be in the form of a carrier as described in embodiments or aspects of the invention herein without an additional capture agent or chemoattractant contained therein or attached thereto. In other embodiments, the carrier may be supplemented by the addition of a further capture agent as described in any of the embodiments or aspects of the invention provided herein. Once the cells are trapped by the capture agent they may then act as a capture agent and/or chemoattractant for other cancer cells.

According to a still further aspect, the invention provides a method of treating or preventing cancer, in particular a metastatic cancer, comprising administering to a subject in need thereof, an agent for modulating tumor cell dissemination, and in particular metastatic tumor cell dissemination, such as circulating tumor cells, disseminated tumor cells or any cell disseminated from a primary tumor. The agent for modulating tumor cell dissemination may be contained within or attached to a carrier. Preferably the subject in need of treatment has already been diagnosed with a primary cancer, both metastatic or not metastatic. Preferably tumor cells are retained or trapped by the action of the agent for modulating tumor cell dissemination. Preferably the method further comprises the step of treating the trapped cells.

According to a still further aspect, the invention provides a method of treating or preventing cancer, in particular a metastatic cancer, comprising administering to a subject in need thereof, a chemoattractant of tumor cells, and in particular metastatic tumor cells, such as circulating tumor cells, disseminated tumor cells or any cell disseminated from a primary tumor. The chemoattractant may be contained within or attached to a carrier. Preferably the subject in need of treatment has already been diagnosed with a primary cancer, both metastatic or not metastatic. Preferably the attracted cells are retained or trapped by the action of the chemoattractant. Preferably the method further comprises the step of treating the attracted cells.

According to a still further aspect, the invention provides a method of treating or preventing cancer, in particular a metastatic cancer, comprising administering to a subject in need thereof, a capture agent for trapping tumor cells, and in particular metastatic tumor cells, such as circulating tumor cells, disseminated tumor cells or any cell disseminated from a primary tumor. The capture agent may be an adhesive to which tumor cells adhere. The capture agent may be in the form of a carrier as described in embodiments or aspects of the invention herein without an additional capture agent or chemoattractant contained therein or attached thereto. In other embodiments, the carrier may be supplemented by the addition of a further capture agent as described in any of the embodiments or aspects of the invention provided herein. Preferably the method further comprises the step of treating the trapped cells. Preferably the subject in need of treatment has already been diagnosed with a primary cancer, both metastatic or not metastatic.

In some embodiments the capture agent comprises a poloxamer polymer hydrogel administered in the absence of any other capture agents contained therein or attached thereto. Alternatively, the capture agent may comprise polystyrene and/or polycaprolactone; or an alginate sponge; or a polycarbonate polyurethane scaffold with urea crosslinks.

The attracted or trapped cells may be treated by physically removing them, for example by surgery, or by treating them to destroy or inactivate the cells, for example by chemotherapy or radiotherapy. If the carrier includes a cytostatic or cytotoxic agent then this may act to eradicate or prevent the replication of the attracted cells. The method may comprise the step of surgically removing the attracted cells, and/or the step of administering chemotherapy and/or radiotherapy to treat the attracted or trapped cells.

The method of the preset invention may be used in combination with current clinical scenarios, including in combination with one or more of surgery, radiotherapy and chemotherapy.

The cancer may be any cancer, in particular a peritoneal cancer, such as ovarian cancer.

According to a still further aspect the invention provides a medical device for use in preventing or, treating cancer, preferably metastatic cancer, in a subject, wherein the device comprises an agent for modulating tumor cell dissemination or a product of the invention.

The skilled man will appreciate that preferred features of any one embodiment and/or aspect and/or claim of the invention may be applied to all other embodiments and/or aspects and/or claims of the invention.

The present invention will be further described in more detail, by way of example only, with reference to the following figures in which:

FIG. 1—illustrates a mouse model of ovarian cancer metastasis. In vivo luminescence images are shown of $1 \times 10^6$ SKOV3 ovarian cancer cells transfected with the luciferase reporter gene injected intraperitoneally into mice. FIG. 1A shows the results without luciferin substrate as control. FIG. 1B shows the pattern of luminescence at the time of injection showing intraperitoneal dissemination of the SKOV3 cells. FIGS. 1C to E show the pattern luminescence one week after injection of the cells, the results show a reproducible pattern of metastasis in the gonadal fat and the pancreas. FIG. 1E shows organ explants showing luciferase positive signals in the pancreas and the gonadal fat.

Figure 2:
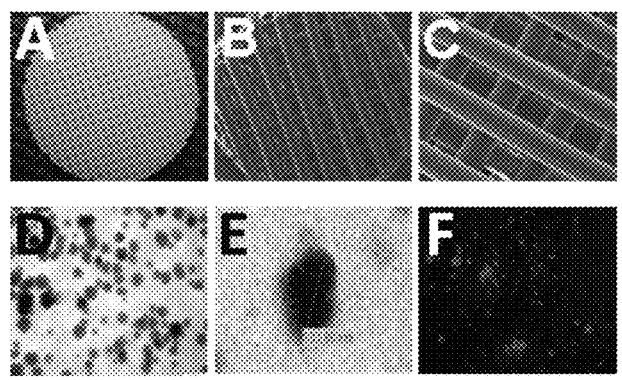

FIG. 2—illustrates a product according to the invention composed of a 3D polymeric scaffold and exosomes. FIGS. 2A to 2C show a 3D InsertTM-PS Nanomesh Tissue Culture Scaffold (3D Biotek, New Jersey, USA), as a platform to contain the exosomes as chemoattractant (magnifications in B and C). FIGS. 2D and 2E show TEM (transmission electron microscopy) images of the microvesicular particles "exosomes" purified by ultracentrifugation from the ascitic fluid of an ovarian cancer patient (magnification in E). FIG. 2F shows exosomes decorated with DID (Octadecylindocarbocyanine), a red fluorescent marker, seeded into the Nanomesh Tissue Culture Scaffold of FIGS. 2A to 2C.

Figure 3:
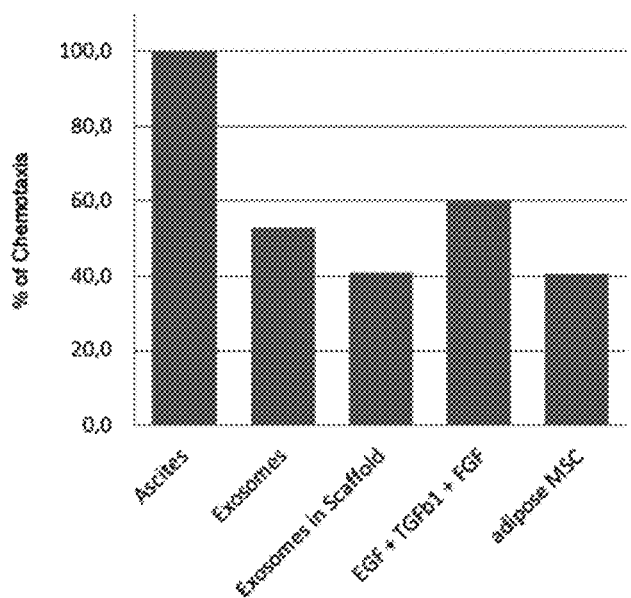

FIG. 3—illustrates graphically a number of agents that promote chemotaxis of SKOV3 cells in vitro. The level of chemotaxis is expressed as a percentage compared to ascitic fluid, the most potent chemoattractant tested. Basically, SKOV3 cells expressing the luciferase reporter gene were induced to migrate through the porous membrane (8 μm) in a Boyden chamber, in response to the indicated chemoattractants. Of note, 1 μg exosomes purified from the ascitic fluid of an ovarian cancer patient demonstrated efficient chemotaxis both in FBS-free media and embedded into the 3D InsertTM-PS scaffold. The combination of the chemokines EGF, TGFb1 and FGF demonstrated a synergistic promotion of chemotaxis. Finally, mesenchymal stem cells of adipose origin were able to induce SKOV3 cells migration in an efficient manner (similar results were obtained with MSC from umbilical and bone marrow origin).

Figure 4:
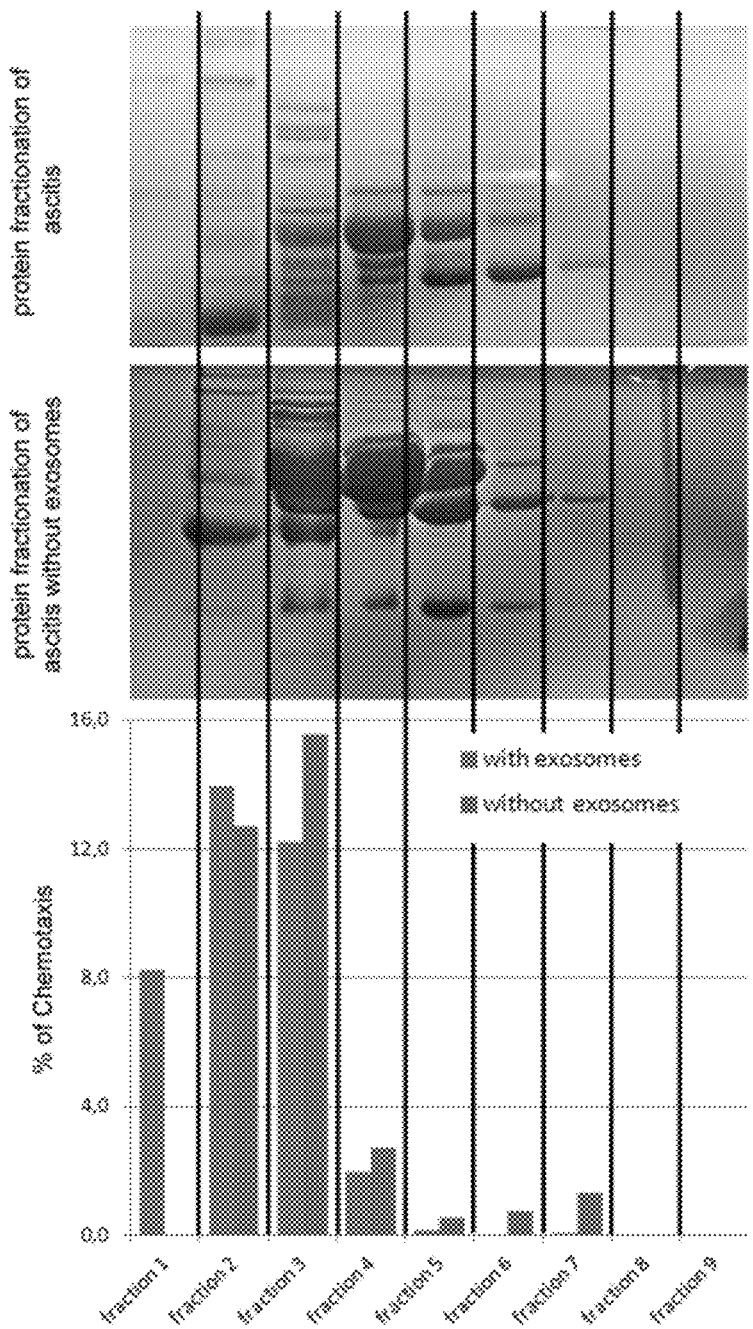

FIG. 4—further demonstrates that exosomes promote chemotaxis of SKOV3 cells. Fractionation of ascitic fluid from an ovarian cancer patient by HPLC (upper panel), and SKOV3 cells migration assays resulted in the first four fractions retaining the capacity of the unfractionated ascitic fluid to promote chemotaxis (the left hand bar in each pair of bars in the lower panel). Depletion of exosomes by ultra-centrifugation was evidenced after fractionation of the ascitic fluid by the complete absence of proteins in the first fraction (middle panel); the concomitant disappearance of chemotaxis in fraction 1 demonstrated the capacity of exosomes purified from the ascitic fluid of ovarian cancer patients to promote chemotaxis.

Figure 5:
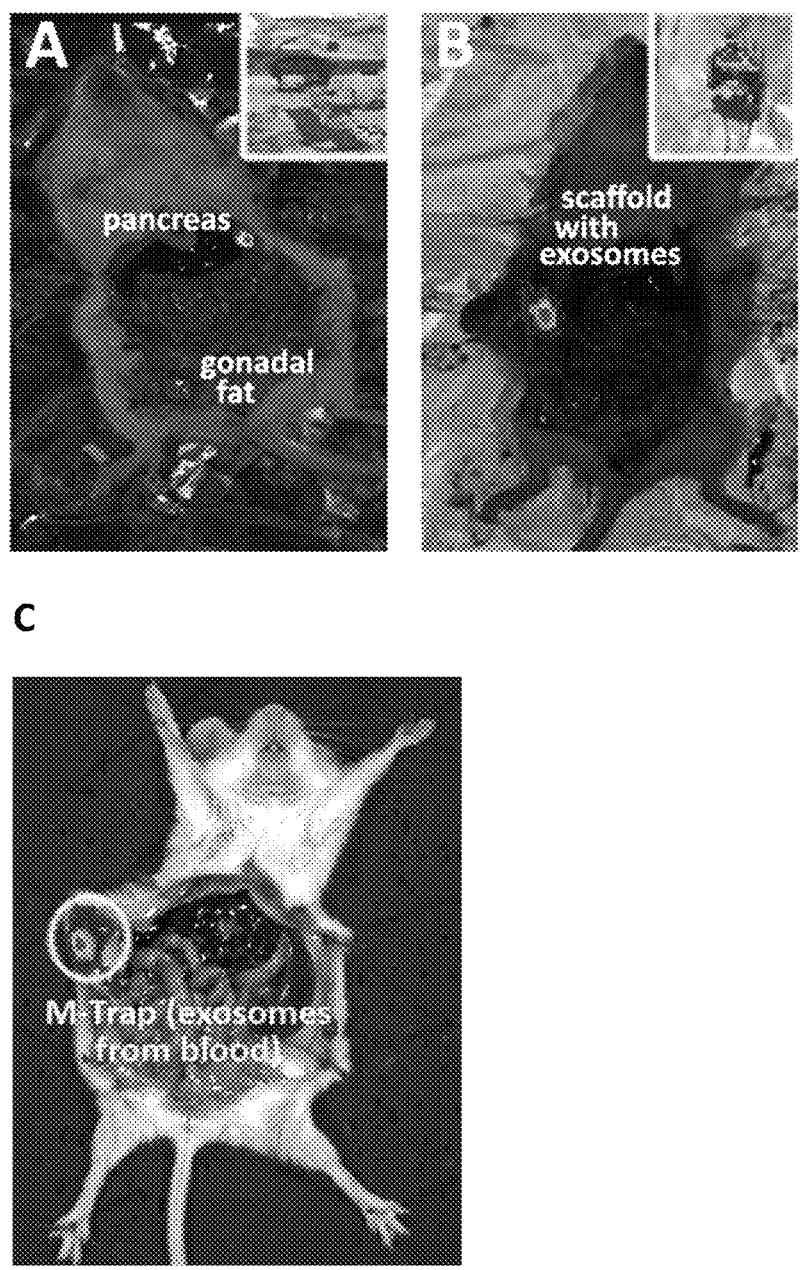

FIG. 5—illustrates a modified pattern of SKOV-3 metastatic cell dissemination in response to ascitic exosomes in a carrier. The figure (A and B) provides an in vivo evaluation of the ability of a scaffold with ascitic exosomes to modulate metastatic tumor cell dissemination. FIG. 5A shows that one week after intraperitoneal injection, $1 \times 10^6$ SKOV3 cells expressing the luciferase reporter gene generated metastasis in the gonadal fat and pancreas (insert in FIG. 5A). FIG. 5B shows that implantation of the scaffold with 50 μg ascitic exosomes in the contra-lateral part of the abdominal wall prevented metastatic dissemination of SKOV3 cells, with a complete disappearance of metastatic foci in the gonadal fat and pancreas and the location of SKVO3 cells within and around the scaffold/trap (insert in FIG. 5B). FIG. 5C shows that the same results were seen when exosomes purified from the blood of healthy individuals were used.

Figure 6:
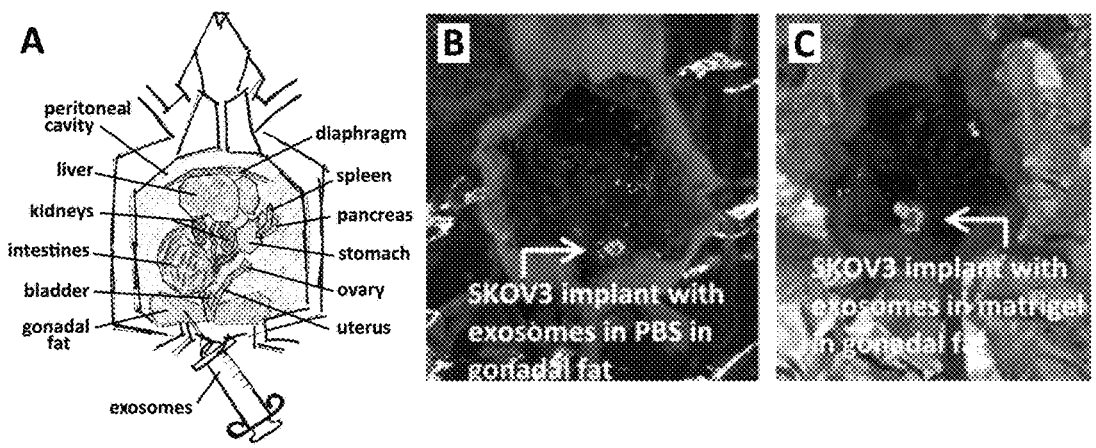

FIG. 6—illustrates a modified pattern of SKOV-3 metastatic cell dissemination with exosomes. The figure provides an in vivo evaluation of the ability of exosomes, resuspended in PBS and Matrigel, to modulate metastatic tumor cell dissemination in the absence of a scaffold. In FIG. 6A exosomes were injected into the gonadal fat and one week later $1 \times 10^6$ SKOV3 cells expressing the luciferase reporter gene were injected intraperitoneally. FIG. 6B illustrates the pattern of tumor cells evaluated by luminescence when mice were sacrificed seven days after SKOV3 cells injection. SKOV3 cells were exclusively localized at the gonadal fat where the exosomes were implanted, with no metastatic focus at the pancreas, compared to control metastatic pattern (see FIG. 5A or 7B). FIG. 6C shows similar results were found when exosomes were embedded into Matrigel as a reservoir, and injected into the gonadal fat.

Figure 7:
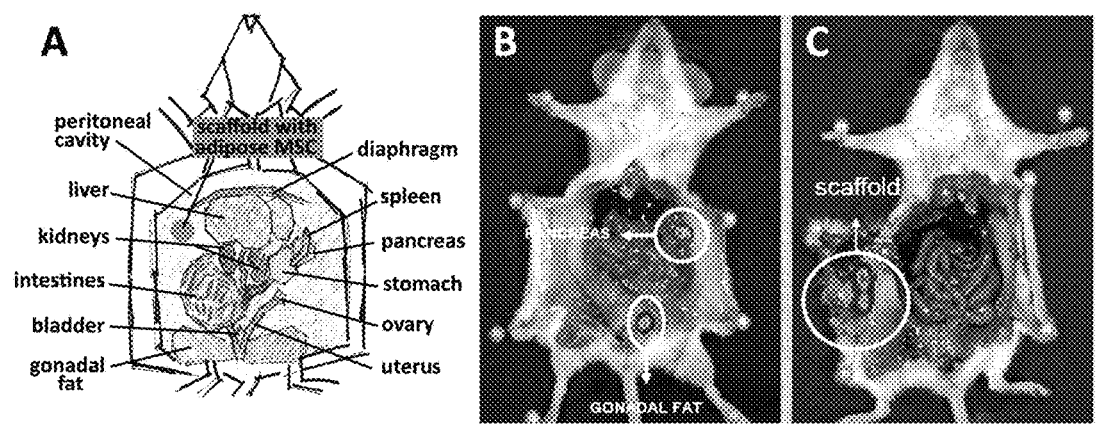

FIG. 7—illustrates a modified pattern of SKOV-3 metastatic cell dissemination with mesenchymal stem cells (MSCs) as a chemoattractant and/or capture agent. The figure provides an in vivo evaluation of the ability of a scaffold with MSCs to attract and capture the metastatic tumor cells. In FIG. 7A adipose MSCs were seeded into the 3D scaffold and surgically implanted into the abdominal wall opposite to the pancreas. One week after intraperitoneal injection, $1 \times 10^6$ SKOV3 cells expressing the luciferase reporter gene generated metastasis in the gonadal fat and pancreas as illustrated in FIG. 7B. In FIG. 7C mice were implanted with a scaffold with 50,000 aMSCs in the contralateral part of the abdominal wall, this had the effect of preventing metastatic dissemination of the SKOV3 cells, with a complete disappearance of metastatic foci in the gonadal fat and pancreas and the location of SKVO3 cells within the scaffold and chemoattractant, a scaffold and chemoattractant is also sometimes referred to as a trap.

Figure 8:
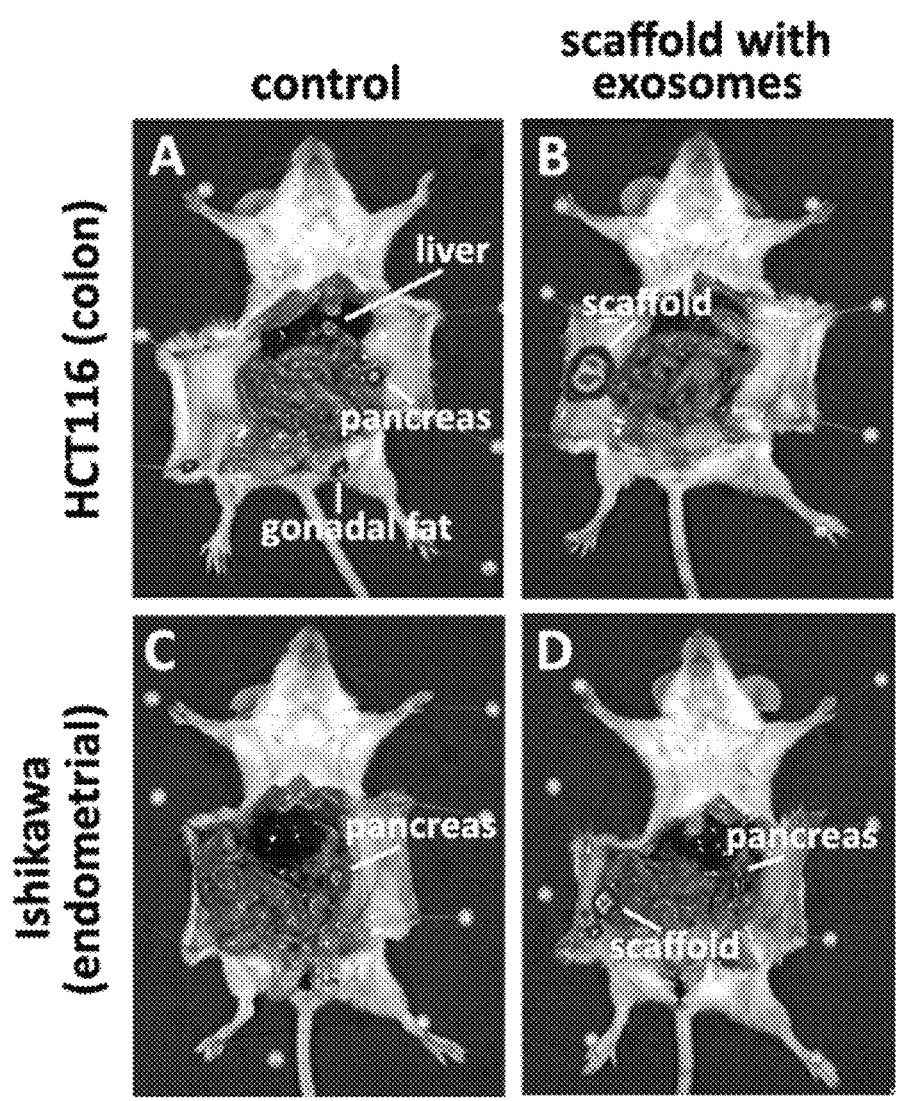

FIG. 8—illustrates a modified pattern of HCT116 and Ishikawa metastatic cell dissemination with exosomes as the chemoattractant and capture agent. The figure provides an in vivo evaluation of the ability of a scaffold with exosomes to attract and capture the metastatic tumor cells. FIG. 8A shows that one week after intraperitoneal injection, $1 \times 10^6$ HCT116 colon cancer cells expressing the luciferase reporter gene generated metastasis mainly at the liver and pancreas, with some cells metastasizing to the gonadal fat. FIG. 8B shows that implantation of a scaffold with exosomes in the contralateral part of the abdominal wall prevented metastatic dissemination of the HCT116 cells, with a complete disappearance of metastatic foci in the liver and pancreas and the location of HCT116 cells within or around the scaffold/trap. Likewise, Ishikawa cells preferentially disseminated to pancreas in the absence of a chemoattractant (FIG. 8C), while most were attracted and/or captured by and located within the trap (scaffold and surrounding area) when injected intraperitoneally in the presence of the scaffold with exosomes (FIG. 8D).

Figure 9:
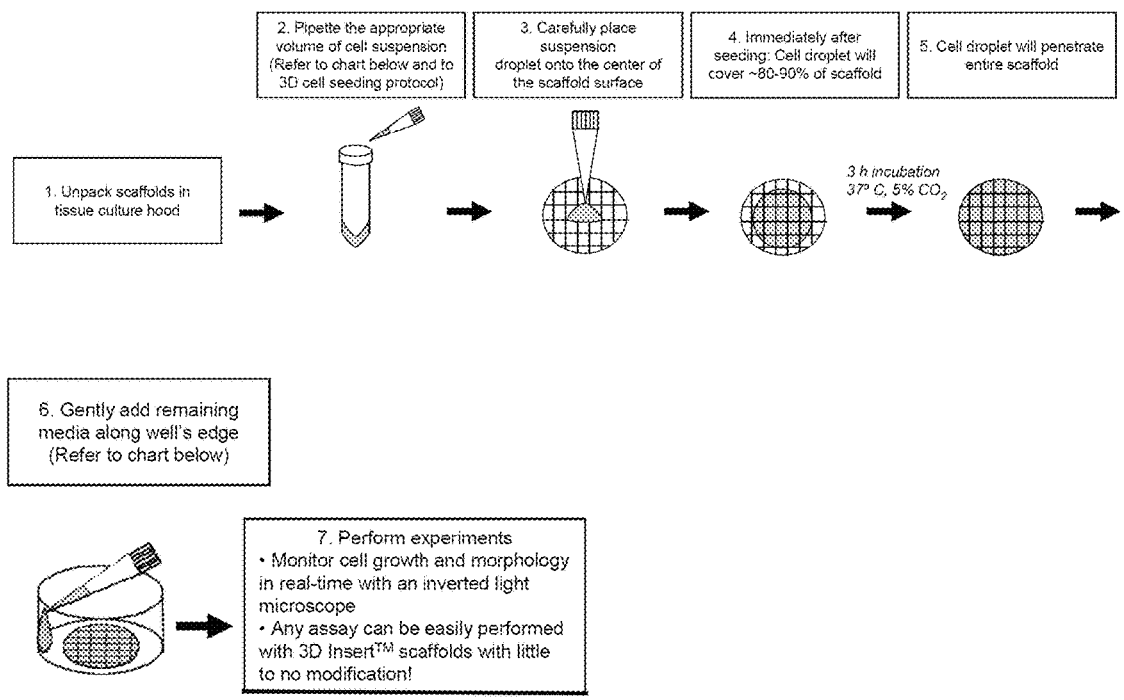
Figure 10:
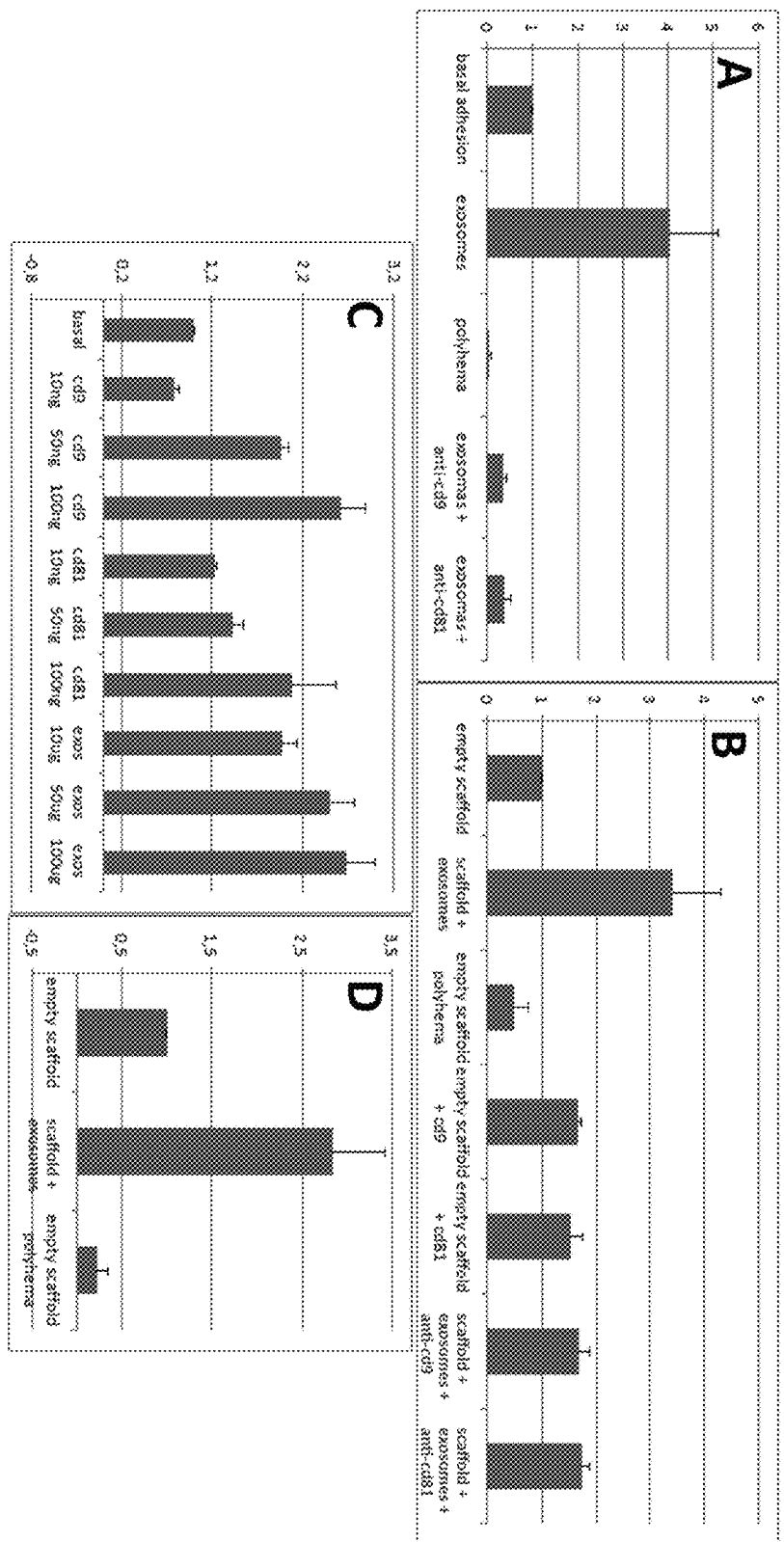

FIG. 9—is a schematic illustration of the seeding of a 3D InsertTM-PS Nanomesh Tissue Culture Scaffold (3D Biotek, New Jersey, USA) with mesenchymal stem cells. The scaffold is made of polystyrene and polycaprolactone FIG. 10—shows exosomes improve adhesion capability of tumor cells to 3D-Biotek scaffolds. Adhesion ability of SKOV3 cells was evaluated in short- and long-term adhesion assays. (a) For short-term adhesion assay, 50,000 SKOV3 cells labelled with calcein were seeded in pretreated 96 well culture plates and 1 hour later cells were washed and those adhered to the plates were quantified by fluorescence. Pre-treatment of wells was as follows: bottom of well plates was decorated with exosomes by passive absorption overnight; alternatively, exosomes were treated with antibodies against CD9 and CD81 for 1 hour, to block the tetraspanin recognition site; finally, polyhema in ethanol (20 mg/ml) was used to cover the bottom of the well to avoid tumor cell adhesion. (b) For long-term adhesion assay, 3D-Biotek scaffolds were pre-treated as above, further including empty scaffolds decorated with 100 ng of both CD9 (empty scaffold+CD9) and CD81 (empty scaffold+ CD81). Reference herein to "M-Trap" refers to a 3D-Biotek scaffold (consisting of polystyrene/polycaprolactone 3D inserts with nanomesh (http://www.3dbiotek.com/web/prod 3dnanomesh.aspx))—decorated with exosomes. Scaffolds were then placed into a 35 mm culture plate, 200.000 calcein-labelled SKOV3 cells were seeded and subjected to orbital movement with the help of a shaker at 37° C. overnight. Scaffolds were recovered and the amount of SKOV3 captured under the different conditions was quantified by fluorescence. (c) Similar adhesion assay as in (b) performed with scaffolds pre-incubated with increasing concentrations (10 ng, 50 ng and 100 ng) of both proteins (cd9 and cd81) overnight at 4° C., and with different concentrations of exosomes (10 mg, 50 μg and 100 μg). (d) Adhesion to M-Trap in dynamic conditions was further evaluated with the help of perfusion pump generating a constant flow of calcein-labelled SKOV3 cells (750 ul/min; see Supplementary FIG. 2). M-Trap, empty scaffold and empty scaffold pre-treated with polyhema to avoid adhesion were subjected to SKOV3 cell flow during 1 hour, and captured SKOV3 cells were quantified by fluorescence.

Figure 11:
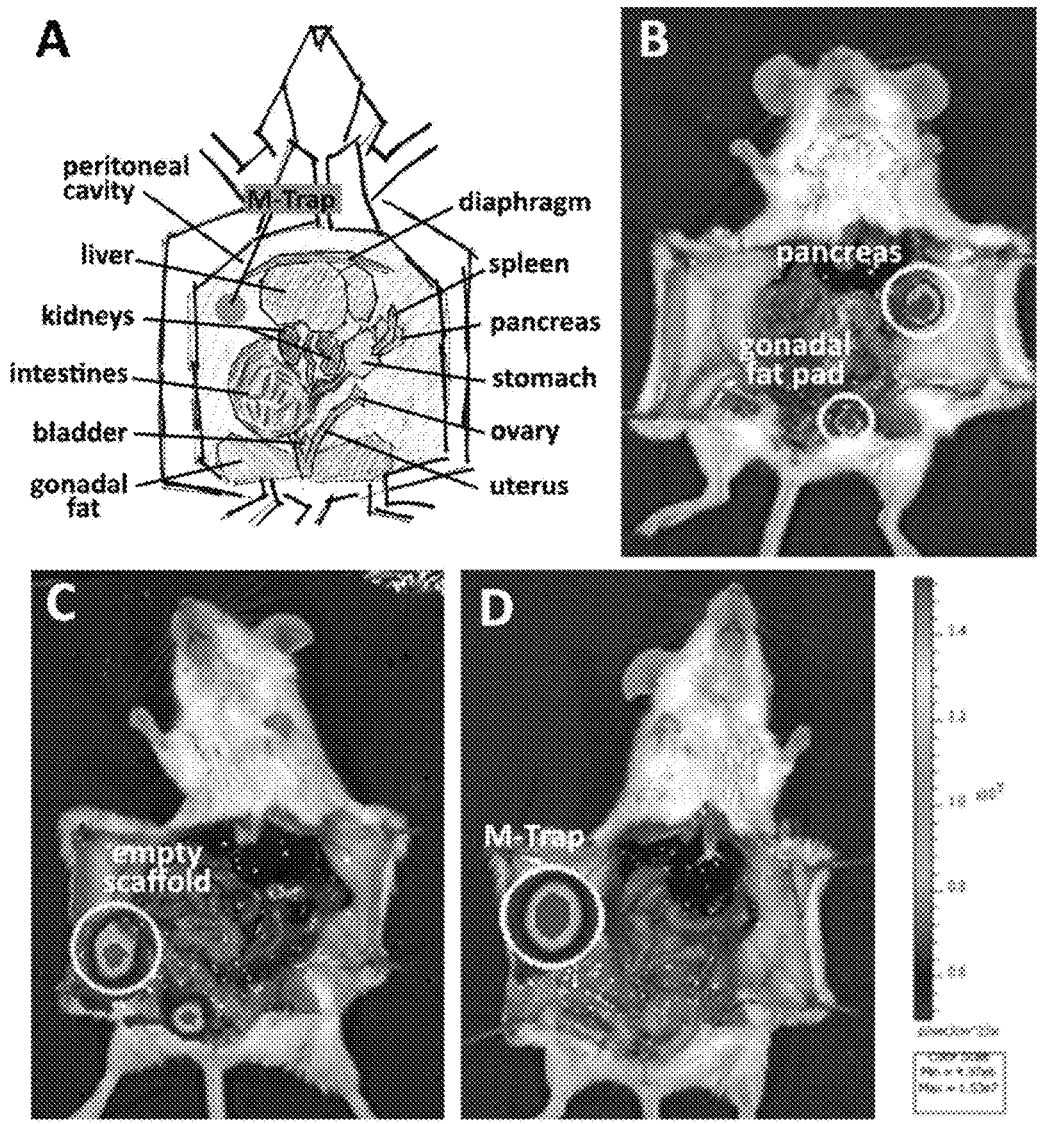

FIG. 11—shows that a device according to the invention, referred to herein as M-Trap (and as described above with reference to FIG. 10), efficiently captures metastaic SKOV3 cells in an in vivo mouse model of peritoneal ovarian metastasis. (a) Scheme of mice peritoneal organs and location of M-Trap opposite to pancreas. (b) One million SKOV3 cells expressing luciferase protein were injected intraperitoneally in mice, and one week later mice were injected with luciferin as substrate of luciferase before sacrifice. Using IVIS technology (In Vivo Imaging System) cells were localized at natural sites of metastasis (pancreas and gonadal fat pad). Empty scaffolds (c) and M-Trap devices (d) were surgically implanted at the inner wall of the peritoneum and 1 week later SKOV3 cells expressing luciferase protein were injected intraperitoneally. After 1 week, the pattern of SKOV3 cells metastasis was analyzed as in (b). Colour scale corresponds to the amount of cells referred to bioluminescence signal. Of note, the natural pattern of ovarian peritoneal metastasis was gradually modulated by adhesion to the empty scaffold and completely remodelled by M-Trap technology.

Figure 12:
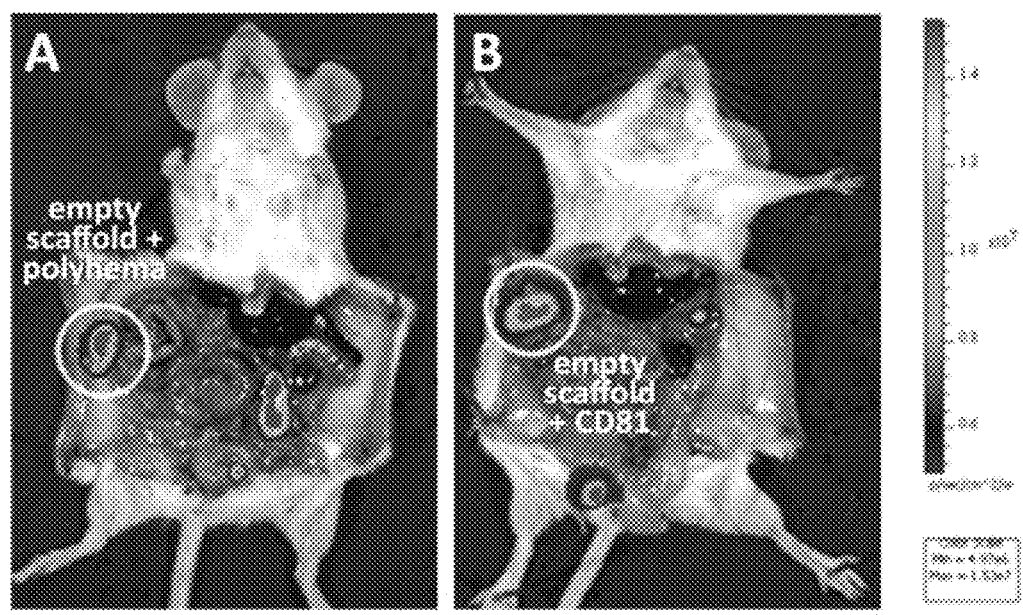

FIG. 12—shows modulation of SKOV3 cells adhesion to 3D-Biotek scaffolds consisting of polystyrene/polycaprolactone 3D inserts with nanomesh. (a) Empty scaffold pretreated with polyhema (20 mg/ml in ethanol) to avoid cell adhesion was implanted at the inner wall of the peritoneum helped by surgical glue. After 1 week, SKOV3 cells expressing luciferase protein were injected intraperitoneally, and 1 week later the mice were sacrificed and visualized for SKOV3 cells metastasis using IVIS technology (In Vivo Imaging System). (b) Similar assay was performed using an empty scaffold incubated overnight at 4° C. with CD81 protein.

Figure 13:
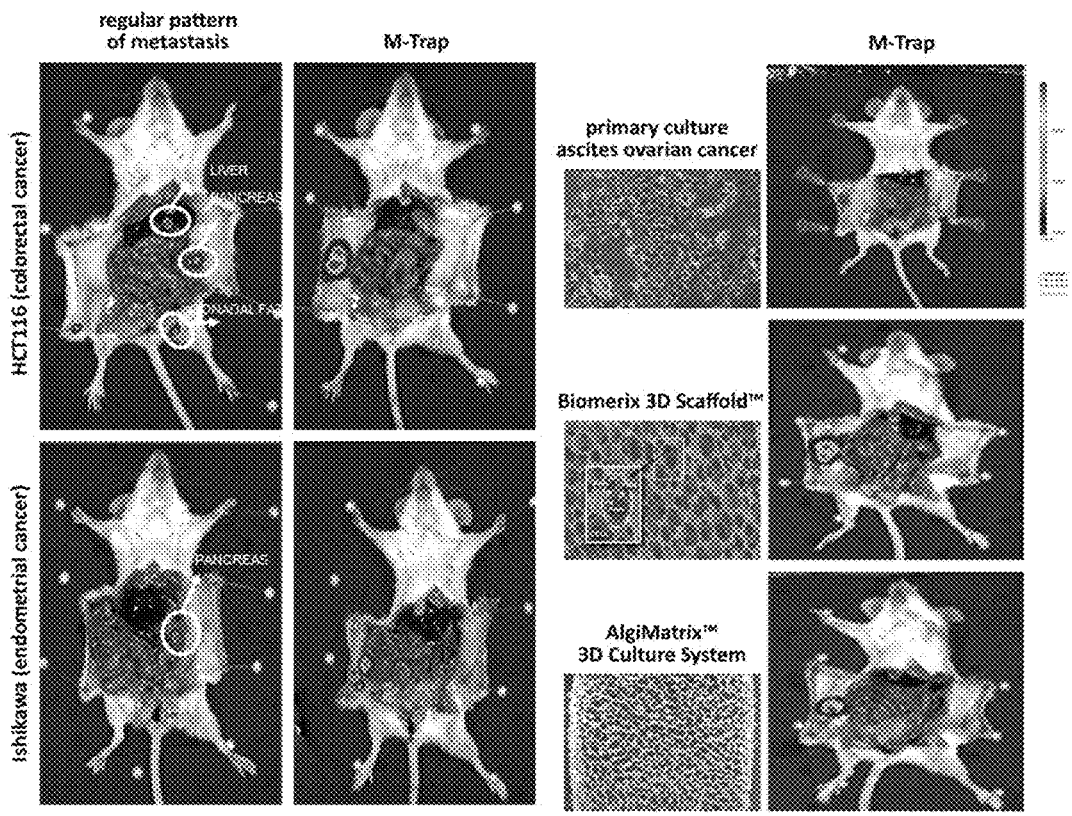

FIG. 13—shows the modulation of peritoneal metastasis in response to primary cultures from ascites of ovarian cancer. In addition to the polystyrene/polycaprolactone scaffold used in K4-trap, several scaffolds were tested to verify their capacity to remodel the pattern of peritoneal metastasis independently of the type of biomaterial. The panels show similar in vivo assays performed with primary culture generated from ascites of ovarian cancer labelled with DiD (upper right panel), to translate into relevant clinical samples the efficiency of the M-Trap polystyrene/polycaprolactone scaffold; and the alternative scaffolds (Biomerix 3D Scaffold, middle right panels; AlgiMatrix 3D Culture System, lower right panels). All the samples tested efficiently captured metastatic tumor cells independently of the biomaterial.

Figure 14:
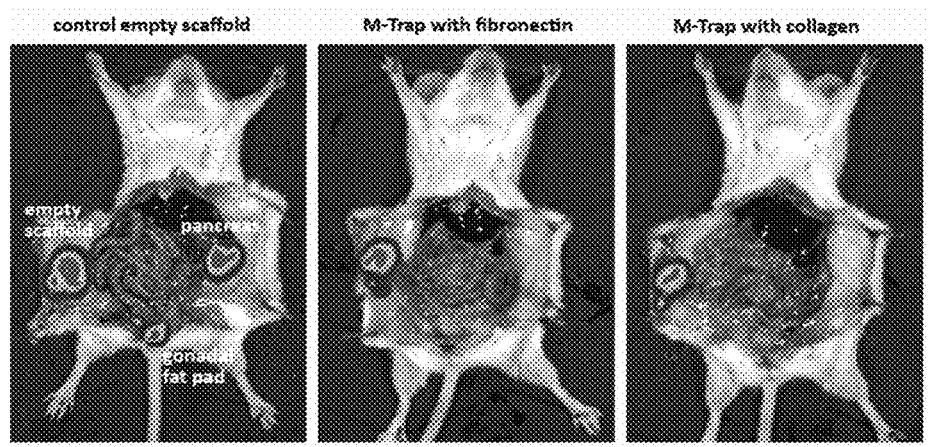

FIG. 14—demonstrates that fibronectin and collagen are effective capture agents in a product of the invention, and that both enhance cellular adhesion to a scaffold. In this example a polystyrene/polycaprolactone scaffold was used.

Figure 15:
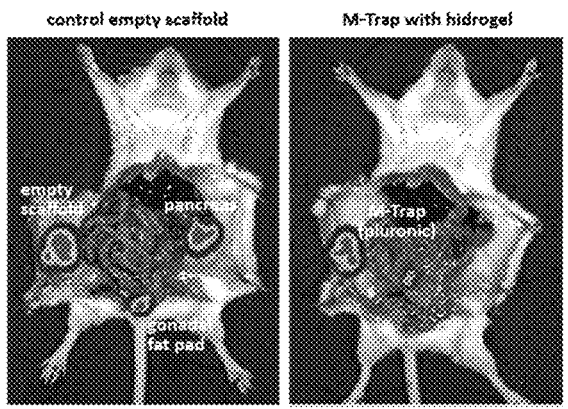

FIG. 15—demonstrates that a hydrogel made of the polymer pluronic on its own is an effective capture agent for metastatic cancer cells.

Figure 16:
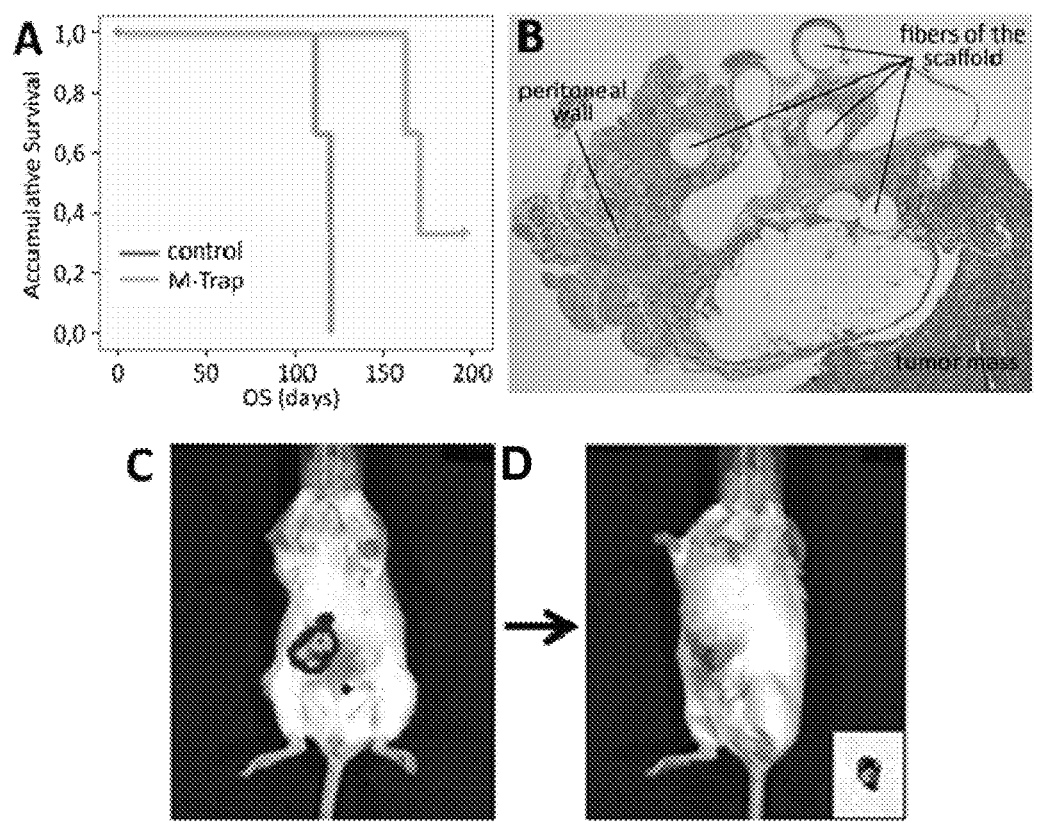

FIG. 16—FIGS. 16A and B demonstrate that a trap of the invention, namely one comprising exosomes and a Biomerix 3D Scaffold (made of a cross-linked, polycarbonate polyurethane-urea matrix), can be used to prolong subject survival times in a mouse ovarian cancer model. FIGS. 16C and D show that a trap of the invention can be removed with the complete eradication of metastatic SKOV3 cells from the peritoneal cavity in a mouse model.

MATERIALS AND METHODS

Exosome Purification and Characterisation.

Exosomes from the ascitic fluid of patients diagnosed with ovarian adenocarcinoma at the University Hospital of Santiago de Compostela were purified by ultracentrifugation. Briefly, 36 ml of ascitic fluid was sequentially centrifuged at 300 g for 10 min, 2,000 g for 20 min, and 10,000 g for 30 min in order to pellet cells and debris. The supernatant was filtered through a 22 micrometers pore-size syringe filter and further centrifuged at 100,000 g for 90 min (SW80 rotor; Beckman Instruments). The resulting pellet was resuspended in 100 ul phosphate-buffered saline, aliquoted and stored at −20° C. Quantification of exosomes was performed by lysis of exososomal proteins by nanodrop and Bradford assay. Exosome size was analyzed at 25° C. with an angle of detection of 90° and laser Doppler anemometry respectively (Zetasizer 3000HS Malvern Instruments). Exosome morphology was evaluated by transmission electron microscopy (TEM) using 10 μL of nanoparticle aqueous suspension.

Trap Device

Products of the invention comprising a carrier and an agent for modulating tumor cell dissemination, or an agent for modulating tumor cell dissemination without a carrier, are also referred to herein as trap devices or traps or M-traps as they serve to "trap" tumor cells. In one example a trap device was made by labelling isolated exosomes with DID (Octadecylindocarbocyanine) a red fluorescent marker, and dropping them into the 3D InsertTM-PS with Nanomesh Tissue Culture Scaffold (3D Biotek, New Jersey, USA). Scaffolds with exosomes were implanted into anesthetized mice by surgical laparotomy and attached to the surface of the abdominal wall with the help of surgical glue (SurgySeal Fibrin Sealant System; BioSTAR, Toronto, Canada).

Alternatively, a trap device was made using 50000 mesenchymal stem cells of adipose origin (hMSC Adip P10763 Innoprot, Bizkaia, Spain) which were seeded into the 3D scaffold by capillarity following manufacturer's instructions (see scheme in FIG. 9), 24 hours before implantation into the mice. The 3D scaffold was the 3D InsertTM-PS with Nanomesh Tissue Culture Scaffold (3D Biotek, New Jersey, USA).

Reference herein to "M-Traps" refers to a 3D-Biotek scaffold consisting of polystyrene/polycaprolactone 3D inserts with nanomesh (http://www.3dbiotek.com/web/prod 3dnanomesh.aspx), typically the K4-trop is decorated with an agent for modulating tumor cell dissemination, such as a capture agent or a chemoattractant.

Mouse Model $1 \times 10^6$ SKOV3 cells, stably expressing a luciferase reporter gene, were resuspended in 200 ml of phosphate buffered saline and injected into the peritoneum of mice. One week after injection, luciferine substrate was administered to the mice by intraperitoneal injection and, after sacrifice, luminicescence imaging in the IVIS Spectrum CT Imaging System was used to determine the pattern of SKOV3 cells metastasis into the peritoneum of the mice.

SKOV3 cells are epithelial cells derived from the ascites of an ovarian adenocarcinoma (for more information: http://www.atcc.org/ATCCAdvancedCatalogSearch/ProductDetails/tabid/452/Default.aspx?ATCCNum=HTB-77&Template=cellBiology).

The mice used are SCID females of 6-8 weeks of age.

An aim of the present invention was to provide a product/trap device which can capture tumour cells, the product or trap device may also act as a potent transmitter of signals which are able to attract to tumor cells. This product would represent a trap for the tumor cells and, by modulating tumor cell dissemination, this product (trap) would prevent the generation of metastatic foci at undesired locations.

Results

Ovarian Cancer Model

The data presented herein proves that in an ovarian cancer model that mimics tumor dissemination a product/trap of the invention can modulate cancer metastasis. In the model, $1 \times 10^6$ SKOV3 ovarian cancer cells are injected intraperitoneally into a mouse which generates a reproducible pattern of metastasis with foci in the pancreas and gonadal fat one week after injection (FIG. 1).

The product of the invention used to capture/trap the metastatic tumor cells was an M-Trap consisting of a 3D InsertTM-PS with Nanomesh Tissue Culture Scaffold (3D Biotek, New Jersey, USA), containing 50 μg of exosomes purified from the ascitic fluid of an ovarian cancer patient (FIG. 2).

The capacity of exosomes to attract and trap SKOV3 cells was demonstrated in vitro in a boyden chamber migration assay. Briefly, 50,000 SKOV3 cells were seeded in the upper compartment and the exosomes were placed in the lower compartment of a boyden chamber. After 24 hours of incubation, the number of SKOV3 cells migrating through the porous membrane due to the gradient of exosome chemoattraction was quantified. As shown in FIG. 3, exosomes efficiently attracted SKOV3 cells compared to the control of culture medium without any chemoattractant. From these results it was concluded that exosomes are efficient chemoattractants of tumor cells and can capture the attracted cells.

The capacity of exosomes to capture SKOV3 cells was demonstrated in vivo using an animal model, where the product of the invention, or M-trap, was composed of a scaffold and exosomes. These experiments demonstrated that the product of the invention was capable of trapping metastatic tumor cells. In the experiments, mice were injected intraperitoneally with $1\times10^6$ SKOV3 cells expressing the luciferase reporter gene for monitoring the efficiency of injection and for the in vivo follow-up of metastasis formation. Mice were injected in the absence or presence of the scaffold with the exosomes implanted in the contralateral part of the abdominal wall. The pancreas was regarded as one of the natural focuses of metastasis in this model. The scaffolds with the exosomes were implanted in the peritoneum by laparotomy with the help of surgical glue (SurgySeal Fibrin Sealant System; BioSTAR, Toronto, Canada), and SKOV3 cells were injected one week after surgery. As shown in FIG. 5, while SKOV3 cells injected intraperitoneally generated metastatic foci in the pancreas and the gonadal fat (FIG. 5A), a unique localization of SKOV3 cells was found within and around the scaffold/trap containing the exosomes as chemoattractant and/or capture agent (FIG. 5B).

These results demonstrated that a trap/product of the invention is capable of interfering with the dissemination of tumor cells, and of attracting and trapping the metastatic cells in a unique localization thus preventing metastasis.

To further demonstrate the efficacy of exosomes to attract and trap tumor cells and prevent the development of metastatic foci by modulating tumor cell dissemination, independently of the scaffold, an in vivo model of metastatic ovarian dissemination was developed in the presence of exosomes injected into the gonadal fat of the mice. For this, exosomes purified from the ascitic fluid of an ovarian cancer patient were resuspended in 100 µl PBS (15 mg of exosomes/ml), and peritoneal surgery was performed to inject the solution of exosomes into the fat located at the base of the uterus of the mice (gonadal fat in FIG. 6A). In this case, the fat represented the carrier of the exosomes. One week later, $1\times10^6$ SKOV3 cells were injected intraperitoneally and seven days later mice were sacrificed to analyse the pattern of metastasis dissemination. As shown in FIG. 6B, exosomes localized at the gonadal fat were able to attract and trap all SKOV3 cells, eliminating the focus of metastasis at the pancreas (see normal pattern of SKOV3 cells dissemination in FIG. 5A or 7B). Similar results were obtained when the purified exosomes were embedded into Matrigel™, an extracellular matrix that provided a semisolid consistency to the exosomes (FIG. 6C); Matrigel with the exosomes may be considered as an alternative to a scaffold with the exosomes.

To assess the validity of the product of the invention/trap device to attract and/or trap tumor cells with other agents for modulating tumor cell dissemination, a product was developed comprising a 3D scaffold seeded with mesenchymal stem cells (MSCs), as an alternative to exosomes. To test the capacity of MSCs to modulate metastatic cell dissemination, a trap device comprising 50,000 MSCs from adipose origin was seeded into the 3D Biotek scaffold 24 hours before implantation in the abdominal wall of the mice (FIG. 7A). As in the previous experiments, seven days after implantation of this alternative product, $1\times10^6$ SKOV3 cells were intraperitoneally injected and one week later the mice were sacrificed and the pattern of metastasis dissemination analyzed. As shown in previous figures, the normal pattern of SKVO3 cells dissemination in this model consists in metastatic focus at the pancreas and in the gonadal fat (FIG. 7B). However, the product composed of MSCs within the 3D scaffold efficiently attracted the SKOV3 cells (FIG. 7C). These results confirmed the capacity of the product/trap device to trap metastatic tumor cells with a different agent for modulating tumor cell dissemination used.

Colon and Endometrial Cancer Model

To assess the validity of the product of the invention/trap device to modulate tumor cell dissemination independent of the type of cancer, the experiments with the 3DBiotek scaffold and exosomes were reproduced using tumor cells of colon (HCT116) and endometrial (Ishikawa) origin, rather than ovarian tumor cells. These two types of cancer also present tumor cell dissemination within the peritoneum.

The scaffold with the exosomes was implanted in the abdominal wall contralateral to the pancreas, as described (FIG. 5; FIG. 7). One week after surgery, $1\times10^6$ HCT116 or Ishikawa cells stably expressing the luciferase reporter gene were intraperitoneally injected and seven days after injection the mice were sacrificed and the pattern of tumor cell dissemination and peritoneal metastasis assessed by luminescence. In parallel, HCT116 or Ishikawa cells were injected in mice without scaffolds to evidence the normal pattern of metastasis. As shown in FIG. 8, colon HCT116 tumor cells mainly metastasized to pancreas and liver (FIG. 8A), while dissemination of endometrial Ishikawa tumor cells preferentially resulted in a unique metastasis focus in the pancreas (FIG. 8C). As observed with the SKOV3 ovarian cancer cells, the pancreas represents a preferential site for the development of metastasis related to peritoneal dissemination in these models. In addition, cell type specific tropisms included the gonadal fat in the case of ovarian tumor cells, and the liver for colon tumor cells.

As with the ovarian cancer, the pattern of metastasis dissemination was completely modified when both HCT116 and Ishikawa cells were injected in the presence of the scaffold with exosomes. The vast majority of cells were localized in and around the scaffold, demonstrating the ability of the trap device composed of a 3D scaffold containing exosomes as chemoattractant to efficiently attract and capture the HCT116 colon cancer cells (FIG. 8B) and the Ishikawa endometrial tumor cells (FIG. 8D). These results demonstrate that the product of the invention/trap device is able to attract and capture metastatic tumor cells independently of the type of cancer.

The Product of the Invention Acts as a Preferential Niche for Implantation and Efficiently Captures Peritoneal Metastatic Cells To confirm whether a product of the invention, exemplified using the M-Trap (a 3D-Biotek scaffold decorated with exosomes as described above) can also behave as a non-pharmacological device, and to demonstrate that one mode of action of the product is to support a preferential implantation (or capture) of metastatic tumor cells, cell adhesion assays were performed both in vitro and in vivo. First, short-term adhesion assays were performed with calcein-labelled SKOV3 cells seeded into wells made of the same polystyrene material as the M-Trap scaffold, and washed after 1 hour of incubation at 37° C.; SKOV3 attached to the bottom of wells were then quantified by fluorescence. As shown in FIG. 10A, SKOV3 cells presented more adhesive capacity in the presence of exosomes decorating the bottom of the well. Moreover, adhesion of SKOV3 cells to exosomes could be partly abolished with antibodies directed against two of the identified exosome proteins previously described to mediate cellular adhesion, the tetraspanins CD9 and CD81, indicative of a specific role of exosomes mediating SKOV3 cells adhesion (FIG. 10A). Next, aiming to mimic in vitro the natural flow of peritoneal fluid within the abdominal cavity, being directed by gravity to its most dependent sites and providing a route for the transcoelomic dissemination of detached tumour cells (Tan et al., Lancet Oncol. 2006; 7:925-34), SKOV3 cells adhesion to an M-Trap device subjected to orbital movement was evaluated (FIG. 10B). Under these dynamic conditions, the preferential implantation of SKOV3 cells in the presence of exosomes was enhanced compared to adhesion to the scaffold and to the scaffold pre-treated with polyhema to avoid adhesion (FIG. 10B). Furthermore, capture of SKOV3 cells by the empty scaffold could be enhanced by decoration with CD9 or CD81 proteins (FIG. 10B), and that of M-Trap diminished by blockage of exosomes with anti-CD9 or anti-CD81 antibodies (FIG. 10B). Moreover, the decoration of the empty scaffold with these two proteins enhanced its adhesion properties in a dose-dependent manner, similar to increased amounts of exosomes (FIG. 10C). Finally, dynamic adhesion of SKOV3 cells to the scaffold pre-treated or not with polyhema and to M-Trap technology was further investigated under perfusion conditions where a constant flow of 750 µl/min tumor cells in suspension was pumped into a chamber where we placed the scaffolds. As shown in FIG. 10D, basal capture of SKOV3 cells into the scaffold due to adhesive properties was further improved in the presence of exosomes. From these results it can be concluded that in vitro, the adhesive capacity of M-Trap technology behaves as a mode of action to capture tumor cells; basal SKOV3 cells adhesion to the 3D-Biotek scaffold being enhanced both with purified exosomes and with exosomal adhesive proteins CD9 and CD81. In addition, the orbital flow mimicking transcoelomic dissemination present in the peritoneal cavity in ovarian cancer metastasis may facilitate the passage and contact of metastatic tumor cells with M-Trap, thus improving its efficiency.

Once characterized in vitro, experiments were undertaken to translate this mode of action of M-Trap to an in vivo mice model of intraperitoneal injection of SKOV3 cells mimicking ovarian cancer dissemination and peritoneal metastasis. For this, M-Trap was surgically implanted at the inner wall of the peritoneum, opposite to the pancreas (scheme in FIG. 11A), and $1 \times 10^6$ SKOV3 cells stably expressing the luciferase reporter gene were injected one week later. Animals were sacrificed one week after intraperitoneal injection, and the pattern of dissemination evaluated by bioluminescence. The pattern of peritoneal metastasis in the absence of scaffold presented two main foci at the pancreas and gonadal fat pad (FIG. 11B). By contrast, in the presence of an empty scaffold without exosomes, an additional foci of SKOV3 cells was observed within the scaffold (FIG. 11C), translating into an in vivo model the capacity of the scaffold to adhere metastatic tumor cells. Remarkably, the pattern of dissemination of the metastatic ovarian tumor cells in the presence of M-Trap device was completely remodelled/modulated, with the eradication of the regular places of metastasis and presenting a unique focus within the scaffold with exosomes (FIG. 11D).

Moreover, when the adhesive capacity of the empty scaffold was limited by a pre-treatment with polyhema, a reduced ability to capture metastatic SKOV3 cells was observed (FIG. 12A). Conversely, when the adhesive capacity of the scaffold was enhanced by decorating it with the tetraspanin CD81, an increased ability to capture metastatic SKOV3 cells was evidenced by the elimination of pancreatic metastasis (FIG. 12B). Similar results were obtained by decorating the scaffold with CD9 tetraspanin (data not shown). From these results it can be concluded that analogous to the in vitro data, a gradual adhesive capacity of scaffolds could be observed resulting in capture of metastatic SKOV3 cells, with polyhema pre-treated scaffolds demonstrating a residual adhesion probably due to a foreign-body inflammatory reaction to biomaterials, a relevant adhesion to the 3D-Biotek scaffold implanted, further improved with the decoration of CD9 or CD81 tetraspanins, and a complete remodelling of the pattern of metastasis with purified exosomes. Globally, these results translated into an in vivo model of ovarian peritoneal metastasis which demonstrated the ability of M-Trap or a trap of the invention to capture disseminating tumor cells, wherein the trap principally acts as a potent artificial pre-metastatic niche where metastatic cells circulating in the peritoneum may adhere preferentially in competition to the natural sites of metastasis implantation.

FIG. 14 further demonstrates the ability of traps according to the invention to capture metastatic SKOV3 cells disseminating through the peritoneum of a mouse model. In this figure 3D-Kube Biomerix scaffolds (wherein the scaffold is made of a non-resorbable, reticulated, cross-linked, polycarbonate polyurethane-urea matrix) decorated with fibronectin and collagen are shown to trap SKOV3 cells in an in vivo model of ovarian peritoneal metastasis.

FIG. 15 also demonstrates the ability of traps according to the invention to capture metastatic SKOV3 cells disseminating through the peritoneum of a mouse model when the trap comprises a scaffold. In this figure a hydrogel made of poloxamers, known as pluronics, was used as the trap. The trap was made by filling an empty 3D-Biotek scaffold with the hydrogel at low temperature to keep it in liquid form. The temperature was then increased to polymerize and solidify the hydrogel. The solidified hydrogel was then introduced into the peritoneum of the mice As can be observed in FIG. 15, this alternative non-biological trap was capable of capturing metastatic cells as efficiently as exosomes.

The efficiency of M-Trap and other products/traps according to the invention to remodel the pattern of metastasis and to transform a disseminated disease into a focalized disease was further demonstrated in a similar model of peritoneal metastasis in colorectal and endometrial cancer. Both are tumors which clinically disseminate through the peritoneal cavity in addition to hepatic and systemic blood and lymphatic spread (FIG. 13). Likewise, primary cultures isolated from ascites of ovarian cancer patients were efficiently captured within the M-Trap/trap devices when injected intraperitoneally in the in vivo model (FIG. 13), further translating the potential of the invention to capture metastatic cells into relevant clinical samples. Finally, exosomes embedded in a porous alginate platform (AlgiMatrix™ 3D Culture System; Gibco™, Invitrogen, Life Technologies, Carlsbad, Calif.) or in a biointegrative scaffold (Biomerix 3D Scaffold™; Biomerix Corporation, Fremont, Calif.) efficiently trapped SKOV3 cells intraperitoneally injected (FIG. 13), demonstrating the competence of the invention is scaffold-independent. All these results demonstrate in an in vivo model the ability of trap devices according to the invention to capture tumor cells, the exosomes within the scaffold generating a preferential site for the homing of metastatic tumor cells disseminating through the peritoneum.

Traps According to the Invention Ameliorate Survival in the Ovarian Metastasis Model The impact of traps according to the invention on survival within an animal model mimicking peritoneal carcinomatosis of ovarian cancer was studied. A control group of animals were injected with $2.5 \times 10^6$ SKOV3 cells intraperitoneally and this was compared to a group of animals previously implanted with a scaffold with exosomes (M-Trap group). The animals were studied with respect to increased morbidity at advanced stages of disease, and the behavior and performance status of the animals, the endpoint being defined as a drop in their weight of 25%. While in the absence of M-Trap technology mice started to lose weight approximately 100 days after SKOV3 cells injection and reached the endpoint and had to be sacrificed at four months, weight of mice implanted with the M-Trap technology started to drop at day 150 and presented a significant accumulative survival (p=0.025; FIG. 16A). These results clearly demonstrated a clinical advantage of the trap technology of the invention in an animal model mimicking peritoneal metastatic dissemination in ovarian cancer.

Remarkably, when the distribution of peritoneal metastasis was analyzed in the M-Trap group, a tumor mass was only found growing within the scaffold. Histological examination of the scaffold showed an infiltrative component of fibroblasts within the scaffold and the implantation of the ovarian tumor cells at the light of the peritoneum (FIG. 16B), without any significant effect on the attraction and capture of metastatic tumor cells. These results further reinforced the trap technology of the invention as an appropriate technology aiming to capture the metastatic tumor cells and to transform a systemic disease into a focalized disease.

Surgical Removal of M-Trap

To evaluate the impact of the trap technology of the invention in a more realistic clinical scenario, an animal treated with a scaffold with exosomes (M-trap) had the scaffold surgically removed once the ovarian metastatic cells have been captured. In this experiment the M-Trap device was surgically implanted as described previously and one week later $2.5 \times 10^6$ SKOV3 cells were intraperitoneally injected. One month after injection, when metastatic tumor cells have been captured and the tumor mass within the M-Trap could be evidenced (left panel in FIG. 16C), the scaffold was removed and mice were followed-up. As can be observed in right panel of FIG. 16C, removal of K4-Trap device resulted in a complete eradication of metastatic SKOV3 cells from the peritoneal cavity.

The invention claimed is:

1. A method of capturing metastatic tumor cells in a subject, comprising administering to the subject an agent comprising: a 2D or 3D porous structure comprised of a non-resorbable polycarbonate polyurethane matrix with urea crosslinks; and collagen protein in or on the matrix, the method further comprising the step of removing or inactivating captured tumor cells.

2. The method of claim 1, wherein the agent is implanted in the peritoneal cavity of the subject.

3. The method of claim 1 wherein the tumor cell is from a cancer selected from the group consisting of breast cancer, colorectal cancer, pancreatic cancer, kidney cancer, prostate cancer, urothelial cancer, oesophageal cancer, head and neck cancer, hepatocellular cancer, mesothelioma, Kaposi's sarcoma, ovarian cancer, soft tissue sarcoma, glioma, melanoma, small-cell and non-small-cell lung cancer, endometrial cancer, basal cell carcinoma, transitional cell carcinoma of the urothelial tract, cervical cancer, endometrial cancer, gastric cancer, bladder cancer, uterine sarcoma, multiple myeloma, soft tissue and bone sarcoma, and cholangiocarcinoma.

4. The method of claim 1 wherein the tumor cell is from a cancer of the peritoneal cavity or a cancer disseminated into the peritoneal cavity.

5. The method of claim 1 wherein the tumor cell is from a cancer selected from the group consisting of kidney cancer, urothelial cancer, urothelial cancer, prostate cancer, ovarian cancer, transitional cell carcinoma of the urothelial tract, cervical cancer, endometrial cancer, colorectal cancer, pancreatic cancer, hepatocellular cancer, hepatocellular cancer, gastric cancer, bladder cancer and uterine sarcoma.

6. The method of claim 1, wherein the matrix further comprises fibronectin.

7. The method of claim 1, wherein the agent further comprises one or more chemotherapeutic agents.

* * * * *